(12) United States Patent
Gjermansen

(10) Patent No.: US 10,030,239 B2
(45) Date of Patent: Jul. 24, 2018

(54) POLYPEPTIDES HAVING PROTEASE ACTIVITY AND POLYNUCLEOTIDES ENCODING SAME

(71) Applicant: Novozymes A/S, Bagsvaerd (DK)

(72) Inventor: Morten Gjermansen, Greve (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 15/039,489

(22) PCT Filed: Dec. 19, 2014

(86) PCT No.: PCT/EP2014/078814
§ 371 (c)(1),
(2) Date: May 26, 2016

(87) PCT Pub. No.: WO2015/091989
PCT Pub. Date: Jun. 25, 2015

(65) Prior Publication Data
US 2017/0029796 A1  Feb. 2, 2017

(30) Foreign Application Priority Data

Dec. 20, 2013 (EP) .................................... 13198809

(51) Int. Cl.
*C12N 9/54* (2006.01)
*C12N 1/20* (2006.01)
*C12N 1/15* (2006.01)

(52) U.S. Cl.
CPC ........ *C12N 9/54* (2013.01); *C12Y 304/21062* (2013.01)

(58) Field of Classification Search
None
See application file for complete search history.

(56) References Cited

U.S. PATENT DOCUMENTS 6,511,371 B2 * 1/2003 Outtrup .................. C11D 3/386
435/219

FOREIGN PATENT DOCUMENTS

WO   2009/019157 A1   2/2009

OTHER PUBLICATIONS

Sang, H., Mechanisms of Development 121:1179-1186, 2004 (Year: 2004).*
Earl et al., UniProt Accession No. E5WNY8 (2011).
Neveu et al., Appl. Microbiol. Biotechnol., vol. 91, No. 3, pp. 635-644 (2011).
Neveu et al., UniProt Accession No. F4ZE70 (2011).
Siezen et al., Protein Science, vol. 6, pp. 501-523 (1997).

* cited by examiner

*Primary Examiner* — David Steadman
(74) *Attorney, Agent, or Firm* — David Fazzolare

(57) ABSTRACT

The present invention relates to isolated polypeptides having protease activity, and polynucleotides encoding the polypeptides. The invention further relates to the use of such polypeptides in detergent and/or in cleaning processes. The invention also relates to nucleic acid constructs, vectors, and host cells comprising the polynucleotides as well as methods of producing the polypeptides.

13 Claims, No Drawings

US 10,030,239 B2

POLYPEPTIDES HAVING PROTEASE ACTIVITY AND POLYNUCLEOTIDES ENCODING SAME

CROSS-REFERENCE TO RELATED APPLICATIONS

This application is a 35 U.S.C. 371 national application of PCT/EP2014/078814 filed Dec. 19, 2014, which claims priority or the benefit under 35 U.S.C. 119 of European application no. 13198809.9 filed Dec. 20, 2013. The contents of these applications are fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to the use of polypeptides having protease activity and polynucleotides encoding the polypeptides. The invention also relates to nucleic acid constructs, vectors, and host cells comprising the polynucleotides as well as methods of producing the polypeptides. The present invention particularly relates to the use of polypeptides having protease activity in food application and in detergents.

Description of the Related Art

Enzymes have been used for many decades in the cleaning compositions such as detergents for various purposes such as laundry and dish wash in house hold care and industrial cleaning. A mixture of different enzymes are used each performing its specific activity to specific substances constituting soil from various stains. Proteases are enzymes which degrade proteins and can be used in cleaning processes such as dish wash and laundry to remove the proteinaceous stains. The most commonly used proteases are the serine proteases, in particular subtilases. This family has previously been further grouped into 6 different sub-groups by Siezen RJ and Leunissen JAM, 1997, Protein Science, 6, 501-523. One of these sub-groups is the subtilisin family which includes subtilases such as SAVINASE®, ALCALASE® (Novozymes A/S) and BLAP® (Henkel AG). Over the years the subtilisins and other proteases has been genetically engineered to increase their performance. Typically the proteases are designed to fulfil different purposes such as to increase their wash performance e.g. at low temperature conditions and/or increase their capacity to remove certain stains. Commercially known genetically engineered proteases includes RELASE®, POLARZYME®, KANNASE®, LIQUANASE®, OVOZYME®, CORONASE®, BLAZE® (Novozymes A/S), PROPERASE®, PURAFECT PRIME®, PURAFECT OX®, FN3®, FN4®, EXCELLASE® and ULTIMASE® (Danisco/DuPont). Despite the availability of many optimized proteases designed for various purposes the compositions of the soiling and stains are very complex and the wash conditions and detergent composition changes to meet different user needs. All factors which makes the availability of different types of proteases for use in cleaning and detergents advantageous.

SUMMARY OF THE INVENTION

The present invention relates to isolated *bacillus* polypeptides having protease activity, selected from the group consisting of:

(a) a polypeptide having at least 85% sequence identity to the mature polypeptide of SEQ ID NO: 2;
(b) a polypeptide encoded by a polynucleotide having at least 85% sequence identity to the mature polypeptide coding sequence of SEQ ID NO: 1;
(c) a variant of the mature polypeptide of SEQ ID NO: 2 comprising a substitution, deletion, and/or insertion at one or more (e.g. several) positions; and
(d) a fragment of the polypeptide of (a), (b) or (c) that has protease activity;
(e) a polypeptide having at least 80% sequence identity to the mature polypeptide of SEQ ID NO: 4;
(f) a polypeptide encoded by a polynucleotide having at least 80% sequence identity to the mature polypeptide coding sequence of SEQ ID NO: 3;
(g) a variant of the mature polypeptide of SEQ ID NO: 4 comprising a substitution, deletion, and/or insertion at one or more (e.g. several) positions; and
(h) a fragment of the polypeptide of (e), (f) or (g) that has protease activity;
(i) a polypeptide having at least 90% sequence identity to the mature polypeptide of SEQ ID NO: 6;
(j) a polypeptide encoded by a polynucleotide having at least 90% sequence identity to the mature polypeptide coding sequence of SEQ ID NO: 5;
(k) a variant of the mature polypeptide of SEQ ID NO: 6 comprising a substitution, deletion, and/or insertion at one or more (e.g. several) positions; and
(l) a fragment of the polypeptide of (i), (j) or (k) that has protease activity.

The present invention also relates to isolated polynucleotides encoding the polypeptides of the present invention; nucleic acid constructs; recombinant expression vectors; recombinant host cells comprising the polynucleotides; and methods of producing the polypeptides.

The present invention also relates to the use of the proteases of the invention in detergent cleaning and detergent compositions, methods of doing cleaning and stain removal processes.

The present invention also relates to a polynucleotide encoding a signal peptide comprising or consisting of amino acids −110 to −84 of SEQ ID NO: 2, a polynucleotide encoding a propeptide comprising or consisting of amino acids −83 to −1 of SEQ ID NO: 2, or a polynucleotide encoding a signal peptide and a propeptide comprising or consisting of amino acids −110 to −1 of SEQ ID NO: 2, each of which is operably linked to a gene encoding a protein; nucleic acid constructs, expression vectors, and recombinant host cells comprising the polynucleotides; and methods of producing a protein.

The present invention also relates to a polynucleotide encoding a signal peptide comprising or consisting of amino acids −103 to −77 of SEQ ID NO: 4, a polynucleotide encoding a propeptide comprising or consisting of amino acids −76 to −1 of SEQ ID NO: 4, or a polynucleotide encoding a signal peptide and a propeptide comprising or consisting of amino acids −103 to −1 of SEQ ID NO: 4, each of which is operably linked to a gene encoding a protein; nucleic acid constructs, expression vectors, and recombinant host cells comprising the polynucleotides; and methods of producing a protein.

The present invention also relates to a polynucleotide encoding a signal peptide comprising or consisting of amino acids −106 to −78 of SEQ ID NO: 6, a polynucleotide encoding a propeptide comprising or consisting of amino acids −77 to −1 of SEQ ID NO: 6, or a polynucleotide encoding a signal peptide and a propeptide comprising or consisting of amino acids −106 to −1 of SEQ ID NO: 6, each of which is operably linked to a gene encoding a protein; nucleic acid constructs, expression vectors, and recombinant host cells comprising the polynucleotides; and methods of producing a protein

OVERVIEW OF SEQUENCE LISTING

SEQ ID NO: 1 is the DNA sequence of *Bacillus* sp-1 protease

SEQ ID NO: 2 is the amino acid sequence as deduced from SEQ ID NO: 1

SEQ ID: NO: 3 is the amino acid sequence of *Bacillus idriensis* protease

SEQ ID NO: 4 is the amino acid sequence as deduced from SEQ ID NO: 3

SEQ ID NO: 5 is the DNA sequence of *Bacillus* sp-2 protease

SEQ ID NO: 6 is the amino acid sequence as deduced from SEQ ID NO: 5

SEQ ID: NO: 7 is the amino acid sequence of the mature *Bacillus* sp-1 protease.

SEQ ID: NO: 8 is the amino acid sequence of the mature *Bacillus idriensis* protease SEQ ID: NO: 9 is the amino acid sequence of the mature *Bacillus* sp-2 protease.

SEQ ID NO 10 is the amino acid sequence of the TY-145 protease (WO2004/067737, SEQ ID NO: 1).

SEQ ID NO: 11 forward primer for *Bacillus* sp-1 protease

SEQ ID NO: 12 reverse primer for *Bacillus* sp-1 protease

SEQ ID NO: 13 forward primer for *Bacillus idriensis* protease

SEQ ID NO: 14 reverse primer for *Bacillus idriensis* protease

SEQ ID NO: 15 forward primer for *Bacillus* sp-2 protease

SEQ ID NO: 16 reverse primer for *Bacillus* sp-2 protease

SEQ ID NO: 17 is the amino acid sequence of *Bacillus lentus*

SEQ ID NO: 18 is the amino acid sequence of *Termomyces lanuginosus*

SEQ ID NO: 19 is the amino acid sequence of *Bacillus* sp

SEQ ID NO: 20 is the amino acid sequence of *Bacillus halmapalus*

SEQ ID NO: 21 is the amino acid sequence of *Bacillus* sp.

SEQ ID NO: 22 is the amino acid sequence of *Cytophaga* sp.

SEQ ID NO: 23 is the amino acid sequence of *Bacillus* sp.

SEQ ID NO: 24 is the amino acid sequence of *Bacillus* sp.

SEQ ID NO: 25 is the amino acid sequence of *Bacillus* sp.

SEQ ID NO: 26 is the *Bacillus clausii* secretion signal

SEQ ID NO: 27 is a poly histidine tag

Definitions

Polypeptides Having Protease Activity

Polypeptides having protease activity, or proteases, are sometimes also designated peptidases, proteinases, peptide hydrolases, or proteolytic enzymes. Proteases may be of the exo-type that hydrolyses peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The term "subtilases" refer to a sub-group of serine protease according to Siezen et al., *Protein Engng.* 4 (1991) 719-737 and Siezen et al. *Protein Science* 6 (1997) 501-523. Serine proteases or serine peptidases is a subgroup of proteases characterised by having a serine in the active site, which forms a covalent adduct with the substrate. Further the subtilases (and the serine proteases) are characterised by having two active site amino acid residues apart from the serine, namely a histidine and an aspartic acid residue. The subtilases may be divided into 6 sub-divisions, i.e. the Subtilisin family, the Thermitase family, the Proteinase K family, the Lantibiotic peptidase family, the Kexin family and the Pyrolysin family. The term "protease activity" means a proteolytic activity (EC 3.4). Proteases of the invention are endopeptidases (EC 3.4.21). There are several protease activity types: The three main activity types are: trypsin-like where there is cleavage of amide substrates following Arg or Lys at P1, chymotrypsin-like where cleavage occurs following one of the hydrophobic amino acids at P1, and elastase-like with cleavage following an Ala at P1. For purposes of the present invention, protease activity is determined according to the procedure described in the Examples below. The proteases of the present invention have at least 20%, e.g., at least 40%, at least 50%, at least 60%, at least 70%, at least 80%, at least 90%, at least 95%, or at least 100% of the protease activity of the mature polypeptide with SEQ ID NO: 7, 8 or 9.

The term "protease activity" means a proteolytic activity (EC 3.4.21.) that catalyzes the hydrolysis of amide bond or a protein by hydrolysis of the peptide bond that link amino acids together in a polypeptide chain. Several assays for determining protease activity are available in the art. For purposes of the present invention, protease activity may be determined using Suc-AAPF-pNA assay as described in the Examples of the present application. The polypeptides of the present invention have at least 20%, e.g., at least 40%, at least 50%, at least 60%, at least 70%, at least 80%, at least 90%, at least 95%, or at least 100% of the protease activity of the mature polypeptide with SEQ ID NO: 7, 8 or 9.

The term "isolated polypeptide" as used herein refers to a polypeptide that is isolated from a source. In one aspect, the polypeptide is at least 20% pure, more preferably at least 40% pure, more preferably at least 60% pure, even more preferably at least 80% pure, most preferably at least 90% pure and even most preferably at least 95% pure, as determined by SDS-PAGE. The term "pure" as used herein, refers to the degree of purity of polypeptide in a sample, composition or the like. Thus, such as at least 95% pure means that no more than 5% of the sample, composition or the like consists of impurities. It is within the knowledge of the skilled person to determine the purity of an isolated polypeptide.

The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 97% pure, more preferably at least 98% pure, even more preferably at least 99%, most preferably at least 99.5% pure, and even most preferably 100% pure by weight of the total polypeptide material present in the preparation. The polypeptides of the present invention are preferably in a substantially pure form. This can be accomplished, for example, by preparing the polypeptide by well-known recombinant methods or by classical purification methods.

The term "mature polypeptide coding sequence" means a polynucleotide that encodes a mature polypeptide having protease activity. In one aspect the mature polypeptide is a polypeptide with SEQ ID NO 7, 8 or 9. In another aspect the mature polypeptide is amino acids 1 to 313 of SEQ ID NO 2, the mature polypeptide is amino acids 1 to 314 of SEQ ID NO 4 or the mature polypeptide is amino acids 1 to 314 of SEQ ID NO 6.

The relatedness between two amino acid sequences or between two nucleotide sequences is described by the parameter "sequence identity". For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. Version 6.1.0 was used. The optional parameters used are gap open penalty of 10, gap extension penalty of 0.5, and the EBLOSUM62 (EMBOSS version of BLOSUM62) substitution matrix. The output of Needle labeled "longest identity" (obtained using the -nobrief option) is used as the percent identity and is calculated as follows:

(Identical Residues×100)/(Length of Alignment Total Number of Gaps in Alignment).

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000), preferably version 3.0.0 or later. Version 6.1.0 was used. The optional parameters used are gap open penalty of 10, gap extension penalty of 0.5, and the EDNAFULL (EMBOSS version of NCBI NUC4.4) substitution matrix. The output of Needle labeled "longest identity" (obtained using the -nobrief option) is used as the percent identity and is calculated as follows:

(Identical Deoxyribonucleotides×100)/(Length of Alignment−Total Number of Gaps in Alignment).

The term "fragment" means a polypeptide having one or more (several) amino acids deleted from the amino and/or carboxyl terminus of a mature polypeptide; wherein the fragment has protease activity.

The term "functional fragment of a polypeptide" or "functional fragment thereof" is used to describe a polypeptide which is derived from a longer polypeptide, e.g., a mature polypeptide, and which has been truncated either in the N-terminal region or the C-terminal region or in both regions to generate a fragment of the parent polypeptide. To be a functional polypeptide the fragment must maintain at least 20%, preferably at least 40%, more preferably at least 50%, more preferably at least 60%, more preferably at least 70%, more preferably at least 80%, even more preferably at least 90%, most preferably at least 95%, and even most preferably at least 100% of the protease activity of the full-length/mature polypeptide.

The term "subsequence" means a polynucleotide having one or more (several) nucleotides deleted from the 5' and/or 3' end of a mature polypeptide coding sequence; wherein the subsequence encodes a fragment having protease activity.

The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The term "variant" means a polypeptide having protease activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position.

The terms "cleaning compositions" and "cleaning formulations," refer to compositions that find use in the removal of undesired compounds from items to be cleaned, such as fabric, carpets, dishware including glassware, contact lenses, hard surfaces such as tiles, zincs, floors, and table surfaces, hair (shampoos), skin (soaps and creams), teeth (mouthwashes, toothpastes), etc. The terms encompasses any materials/compounds selected for the particular type of cleaning composition desired and the form of the product (e.g., liquid, gel, granule, powder, or spray compositions), as long as the composition is compatible with the protease and other enzyme(s) used in the composition. The specific selection of cleaning composition materials is readily made by considering the surface, item or fabric to be cleaned, and the desired form of the composition for the cleaning conditions during use. These terms further refer to any composition that is suited for cleaning, bleaching, disinfecting, and/or sterilizing any object and/or surface. It is intended that the terms include, but are not limited to detergent composition (e.g., liquid and/or solid laundry detergents and fine fabric detergents; hard surface cleaning formulations, such as for glass, wood, ceramic and metal counter tops and windows; carpet cleaners; oven cleaners; fabric fresheners; fabric softeners; and textile and laundry pre-spotters, as well as dish detergents).

The term "detergent composition", includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types.

The term "detergent composition", includes unless otherwise indicated, granular or powder-form all-purpose or heavy-duty washing agents, especially cleaning detergents; liquid, gel or paste-form all-purpose washing agents, especially the so-called heavy-duty liquid (HDL) types; liquid fine-fabric detergents; hand dishwashing agents or light duty dishwashing agents, especially those of the high-foaming type; machine dishwashing agents, including the various tablet, granular, liquid and rinse-aid types for household and institutional use; liquid cleaning and disinfecting agents, including antibacterial hand-wash types, cleaning bars, soap bars, mouthwashes, denture cleaners, car or carpet shampoos, bathroom cleaners; hair shampoos and hair-rinses; shower gels, foam baths; metal cleaners; as well as cleaning auxiliaries such as bleach additives and "stain-stick" or pre-treat types. The terms "detergent composition" and "detergent formulation" are used in reference to mixtures which are intended for use in a wash medium for the cleaning of soiled objects. In some embodiments, the term is used in reference to laundering fabrics and/or garments (e.g., "laundry detergents"). In alternative embodiments, the term refers to other detergents, such as those used to clean dishes, cutlery, etc. (e.g., "dishwashing detergents"). It is not intended that the present invention be limited to any particular detergent formulation or composition. The term "detergent composition" is not intended to be limited to compositions that contain surfactants. It is intended that in addition to the polypeptides having protease activity i.e. proteases according to the invention, the term encompasses detergents that may contain, e.g., surfactants, builders, chelators or chelating agents, bleach system or bleach components, polymers, fabric conditioners, foam boosters, suds suppressors, dyes, perfume, tarnish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "fabric" encompasses any textile material. Thus, it is intended that the term encompass garments, as well as fabrics, yarns, fibers, non-woven materials, natural materials, synthetic materials, and any other textile material.

The term "textile" refers to woven fabrics, as well as staple fibers and filaments suitable for conversion to or use as yarns, woven, knit, and non-woven fabrics. The term encompasses yarns made from natural, as well as synthetic (e.g., manufactured) fibers. The term, "textile materials" is a general term for fibers, yarn intermediates, yarn, fabrics, and products made from fabrics (e.g., garments and other articles).

The term "non-fabric detergent compositions" include non-textile surface detergent compositions, including but not limited to compositions for hard surface cleaning, such as dishwashing detergent compositions, oral detergent compositions, denture detergent compositions, and personal cleansing compositions.

The term "effective amount of enzyme" refers to the quantity of enzyme necessary to achieve the enzymatic activity required in the specific application, e.g., in a defined detergent composition. Such effective amounts are readily ascertained by one of ordinary skill in the art and are based on many factors, such as the particular enzyme used, the cleaning application, the specific composition of the detergent composition, and whether a liquid or dry (e.g., granular, bar) composition is required, and the like. The term "effective amount" of a protease refers to the quantity of protease described hereinbefore that achieves a desired level of enzymatic activity, e.g., in a defined detergent composition.

The term "water hardness" or "degree of hardness" or "dH" or "° dH" as used herein refers to German degrees of hardness. One degree is defined as 10 milligrams of calcium oxide per liter of water.

The term "relevant washing conditions" is used herein to indicate the conditions, particularly washing temperature, time, washing mechanics, detergent concentration, type of detergent and water hardness, actually used in households in a detergent market segment.

The term "adjunct materials" means any liquid, solid or gaseous material selected for the particular type of detergent composition desired and the form of the product (e.g., liquid, granule, powder, bar, paste, spray, tablet, gel, or foam composition), which materials are also preferably compatible with the protease enzyme used in the composition. In some embodiments, granular compositions are in "compact" form, while in other embodiments, the liquid compositions are in a "concentrated" form.

The term "stain removing enzyme" as used herein, describes an enzyme that aids the removal of a stain or soil from a fabric or a hard surface. Stain removing enzymes act on specific substrates, e.g., protease on protein, amylase on starch, lipase and cutinase on lipids (fats and oils), pectinase on pectin and hemicellulases on hemicellulose. Stains are often depositions of complex mixtures of different components which either results in a local discolouration of the material by itself or which leaves a sticky surface on the object which may attract soils dissolved in the washing liquor thereby resulting in discolouration of the stained area. When an enzyme acts on its specific substrate present in a stain the enzyme degrades or partially degrades its substrate thereby aiding the removal of soils and stain components associated with the substrate during the washing process. For example, when a protease acts on a grass stain it degrades the protein components in the grass and allows the green/brown colour to be released during washing.

The term "reduced amount" means in this context that the amount of the component is smaller than the amount which would be used in a reference process under otherwise the same conditions. In a preferred embodiment the amount is reduced by, e.g., at least 5%, such as at least 10%, at least 15%, at least 20% or as otherwise herein described.

The term "low detergent concentration" system includes detergents where less than about 800 ppm of detergent components is present in the wash water. Asian, e.g., Japanese detergents are typically considered low detergent concentration systems.

The term "medium detergent concentration" system includes detergents wherein between about 800 ppm and about 2000 ppm of detergent components is present in the wash water. North American detergents are generally considered to be medium detergent concentration systems.

The term "high detergent concentration" system includes detergents wherein greater than about 2000 ppm of detergent components is present in the wash water. European detergents are generally considered to be high detergent concentration systems.

The term "vegetable oil" includes plant oil e.g. oils from plant seeds. Vegetable fats and oils are lipid materials derived from plants. The oil is composed of triglycerides and can also contain minor constituents of phospholipids and galactolipids. Although many plant parts may yield oil in commercial practice, oil is extracted primarily from seeds. Vegetable fats and oils may or may not be edible. Examples of vegetable oils include but are not limited to rapeseed oil, linseed oil, tung oil, castor oil, soy oil, canola oil, sunflower oil, safflower oil, peanut oil, cotton seed oil, palm oil, palm kernel oil, coconut oil, olive oil, grape seed oil, corn oil, sesame oil, algae oil and rice bran oil. The term also includes biodiesel oil, produced from vegetable oil- or animal based oil consisting of long-chain alkyl (methyl, propyl or ethyl) esters by reacting the oil with alcohol to produce fatty acid esters. Thus, the invention includes processing of vegetable oil to produce biodiesel.

DETAILED DESCRIPTION OF THE INVENTION

In one aspect, the present invention relates to an isolated polypeptide having protease activity, selected from the group consisting of: (a) a polypeptide having at least 85% sequence identity to the mature polypeptide of SEQ ID NO: 2; a polypeptide having at least 80% sequence identity to the mature polypeptide of SEQ ID NO: 4; a polypeptide having at least 89% sequence identity to the mature polypeptide of SEQ ID NO: 6; (b) a polypeptide encoded by a polynucleotide having at least 85% sequence identity to the mature polypeptide coding sequence of SEQ ID NO: 1; a polypeptide encoded by a polynucleotide having at least 80% sequence identity to the mature polypeptide coding sequence of SEQ ID NO: 3; a polypeptide encoded by a polynucleotide having at least 89% sequence identity to the mature polypeptide coding sequence of SEQ ID NO: 5; (c) a variant of the mature polypeptide of SEQ ID NO: 2, 4 or 6 comprising a substitution, deletion, and/or insertion at one or more (e.g. several) positions; and (d) a fragment of the polypeptide of (a), (b) or (c) that has protease activity.

In a particular aspect, the present invention relates to an isolated polypeptide having a sequence identity to the mature polypeptide of SEQ ID NO: 2 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptide differ by no more than 20 amino acids, e.g., 1, 2, 3, 4, 5, 6, 7, 8, 9, 10, 11, 12, 13, 14, 15, 16, 17, 18 or 19 from the mature polypeptide of SEQ ID NO: 2.

Another aspect of the present invention relates to an isolated polypeptide having a sequence identity to the mature polypeptide of SEQ ID NO: 4 of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one aspect, the polypeptide differ by no more than 20 amino acids, e.g., 1, 2, 3, 4, 5, 6, 7, 8, 9, 10, 11, 12, 13, 14, 15, 16, 17, 18 or 19 from the mature polypeptide of SEQ ID NO: 4.

Another aspect of the present invention relates to an isolated polypeptide having a sequence identity to the mature polypeptide of SEQ ID NO: 6 of at least 90%, at least 91%, at least 92%, at least 93%, at least 94%, at least 95%, at least 96%, at least 97%, at least 98%, at least 99%, or 100%, which have protease activity. In one aspect, the polypeptide differ by no more than 20 amino acids, e.g., 1, 2, 3, 4, 5, 6, 7, 8, 9, 10, 11, 12, 13, 14, 15, 16, 17, 18 or 19 from the mature polypeptide of SEQ ID NO: 6.

In one embodiment, the polypeptide comprises or consists of SEQ ID NO: 2, 4, 6, or the mature polypeptide of SEQ ID NO: 2, 4, or 6. In another embodiment, A polypeptide of the present invention preferably comprises or consists of the amino acid sequence of SEQ ID NO: 2 or an allelic variant thereof; or is a fragment thereof having protease activity. In another embodiment, the polypeptide comprises or consists of the mature polypeptide of SEQ ID NO: 2. In another embodiment, the polypeptide comprises or consists of amino acids 1 to 313 of SEQ ID NO: 2

A polypeptide of the present invention preferably comprises or consists of the amino acid sequence of SEQ ID NO: 4 or an allelic variant thereof; or is a fragment thereof having protease activity. In another embodiment, the polypeptide comprises or consists of the mature polypeptide of SEQ ID NO: 4. In another embodiment, the polypeptide comprises or consists of amino acids 1 to 314 of SEQ ID NO: 4.

A polypeptide of the present invention preferably comprises or consists of the amino acid sequence of SEQ ID NO: 6 or an allelic variant thereof; or is a fragment thereof having protease activity. In another embodiment, the polypeptide comprises or consists of the mature polypeptide of SEQ ID NO: 6. In another embodiment, the polypeptide comprises or consists of amino acids 1 to 314 of SEQ ID NO: 6.

A particular embodiment the polypeptide having a sequence identity to a polypeptide with SEQ ID NO: 7 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one embodiment, the polypeptide differs by no more than 20 amino acids, e.g., 1, 2, 3, 4, 5, 6, 7, 8, 9, 10, 11, 12, 13, 14, 15, 16, 17, 18 or 19 from the mature polypeptide of SEQ ID NO: 2.

A particular embodiment the polypeptide having a sequence identity to a polypeptide with SEQ ID NO: 8 of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%, which have protease activity. In one embodiment, the polypeptide differs by no more than 20 amino acids, e.g., 1, 2, 3, 4, 5, 6, 7, 8, 9, 10, 11, 12, 13, 14, 15, 16, 17, 18 or 19 from the mature polypeptide of SEQ ID NO: 8.

A particular embodiment, the polypeptide having a sequence identity to a polypeptide with SEQ ID NO: 9 of at least 90%, at least 91%, at least 92%, at least 93%, at least 94%, at least 95%, at least 96%, at least 97%, at least 98%, at least 99%, or 100%, which have protease activity. In one embodiment, the polypeptide differs by no more than 20 amino acids, e.g., 1, 2, 3, 4, 5, 6, 7, 8, 9, 10, 11, 12, 13, 14, 15, 16, 17, 18 or 19 from the mature polypeptide of SEQ ID NO: 9.

In one embodiment, the present invention relates to an isolated polypeptide having protease activity encoded by a polynucleotide that hybridizes under very low stringency conditions, low stringency conditions, medium stringency conditions, medium-high stringency conditions, high stringency conditions, or very high stringency conditions with the mature polypeptide coding sequence of SEQ ID NO: 1, 3 or 5 or the full-length complement thereof (Sambrook et al., 1989, *Molecular Cloning, A Laboratory Manual*, 2d edition, Cold Spring Harbor, New York).

The polynucleotides of SEQ ID NO: 1, 3, 5 or a subsequence thereof, as well as the polypeptides of SEQ ID NO: 2, 4, 6 or a fragment thereof may be used to design nucleic acid probes to identify and clone DNA encoding polypeptides having protease activity from strains of different genera or species according to methods well-known in the art. In particular, such probes can be used for hybridization with the genomic DNA or cDNA of a cell of interest, following standard Southern blotting procedures, in order to identify and isolate the corresponding gene therein. Such probes can be considerably shorter than the entire sequence, but should be at least 15, e.g., at least 25, at least 35, or at least 70 nucleotides in length. Preferably, the nucleic acid probe is at least 100 nucleotides in length, e.g., at least 200 nucleotides, at least 300 nucleotides, at least 400 nucleotides, at least 500 nucleotides, at least 600 nucleotides, at least 700 nucleotides, at least 800 nucleotides, or at least 900 nucleotides in length. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

A genomic DNA or cDNA library prepared from such other strains may be screened for DNA that hybridizes with the probes described above and encodes a polypeptide having protease activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that hybridizes with SEQ ID NO: 1, 3, 5 or a subsequence thereof, the carrier material is used in a Southern blot.

For purposes of the present invention, hybridization indicates that the polynucleotide hybridizes to a labeled nucleic acid probe corresponding to (i) SEQ ID NO: 1, 3 or 5; (ii) the mature polypeptide coding sequence of SEQ ID NO: 1, 3 or 5; (iii) the full-length complement thereof; or (iv) a subsequence thereof; under very low to very high stringency conditions. Molecules to which the nucleic acid probe hybridizes under these conditions can be detected using, for example, X-ray film or any other detection means known in the art.

In one embodiment, the nucleic acid probe is nucleotides 501 to 1769, nucleotides 600 to 1600, nucleotides 700 to 1500, or nucleotides 800 to 1200 of SEQ ID NO: 1. In another embodiment, the nucleic acid probe is a polynucleotide that encodes the polypeptide of SEQ ID NO: 2; the mature polypeptide thereof; or a fragment thereof. In another embodiment, the nucleic acid probe is SEQ ID NO: 1.

In another embodiment, the nucleic acid probe is nucleotides 501 to 1751, nucleotides 600 to 1600, nucleotides 700 to 1500, or nucleotides 800 to 1200 of SEQ ID NO: 3. In another embodiment, the nucleic acid probe is a polynucleotide that encodes the polypeptide of SEQ ID NO: 4; the mature polypeptide thereof; or a fragment thereof. In another embodiment, the nucleic acid probe is SEQ ID NO: 3.

In another embodiment, the nucleic acid probe is nucleotides 501 to 1760, nucleotides 600 to 1600, nucleotides 700 to 1500, or nucleotides 800 to 1200 of SEQ ID NO: 5. In another embodiment, the nucleic acid probe is a polynucleotide that encodes the polypeptide of SEQ ID NO: 6; the mature polypeptide thereof; or a fragment thereof. In another embodiment, the nucleic acid probe is SEQ ID NO: 5.

In another embodiment, the present invention relates to an isolated polypeptide having protease activity encoded by a polynucleotide having a sequence identity to the mature polypeptide coding sequence of SEQ ID NO: 1 of at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to an isolated polypeptide having protease activity encoded by a polynucleotide having a sequence identity to the mature polypeptide coding sequence of SEQ ID NO: 3 of at least 80%, at least 81%, at least 82%, at least 83%, at least 84% at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In another embodiment, the present invention relates to an isolated polypeptide having protease activity encoded by a polynucleotide having a sequence identity to the mature polypeptide coding sequence of SEQ ID NO: 5 of at least 90%, at least 91%, at least 92%, at least 93%, at least 94%, at least 95%, at least 96%, at least 97%, at least 98%, at least 99%, or 100%.

In another embodiment, the present invention relates to variants of the mature polypeptides of SEQ ID NO: 2, 4 or 6 comprising a substitution, deletion, and/or insertion at one or more (e.g., several) positions. In an embodiment, the number of amino acid substitutions, deletions and/or insertions introduced into the mature polypeptides of SEQ ID NO: 2, 4 or 6 is not more than 20, e.g., 1, 2, 3, 4, 5, 6, 7, 8, 9, 10, 11, 12, 13, 14, 15, 16, 17, 18, or 19. The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain. In another embodiment, the number of amino acid substitutions, deletions, and/or insertions introduced into the mature polypeptide if SEQ ID NO:2, 4, or 6, is not more than 40, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, or 39.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, *In, The Proteins*, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for protease activity to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, Science 255: 306-312; Smith et al., 1992, *J. Mol. Biol.* 224: 899-904; Wlodaver et al., 1992, *FEBS Lett.* 309: 59-64. The identity of essential amino acids can also be inferred from an alignment with a related polypeptide. The identity of essential amino acids can also be inferred from an alignment with a related polypeptide. For the polypeptide with SEQ ID NO 2 the catalytic triad comprising the amino acids D37, H74 and S253 is essential for protease activity of the enzyme.

For the polypeptide with SEQ ID NO: 4, the catalytic triad comprising the amino acids D38, H75 and S254 is essential for protease activity of the enzyme.

For the polypeptide with SEQ ID NO: 6, the catalytic triad comprising the amino acids D38, H75 and S254 is essential for protease activity of the enzyme.

In an embodiment, the variant has improved catalytic activity compared to the parent enzyme.

In a particular embodiment, the variant has at least 10%, such as at least 15%, such as at least 20%, such as at least 30%, improved catalytic activity compared to the parent enzyme.

Single or multiple amino acid substitutions, deletions, and/or insertions may be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochemistry* 30: 10832-10837; U.S. Pat. No. 5,223,409; WO 92/06204), and region-directed mutagenesis (Derbyshire et al., 1986, *Gene* 46: 145; Ner et al., 1988, *DNA* 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide may further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, *Proteins: Structure, Function, and Genetics* 6: 240-248; and Stevens, 2003, *Drug Discovery World* 4: 35-48.

Sources of Polypeptides Having Protease Activity

Polypeptides having protease activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptides may be a bacterial protease. For example, the polypeptides may be a Gram-positive bacterial polypeptide such as a *Bacillus*, *Clostridium*, *Enterococcus*, *Geobacifius*, *Lactobacillus*, *Lactococcus*, *Oceanobacillus*, *Staphylococcus*, *Streptococcus*, or *Streptomyces* protease, or a Gram-negative bacterial polypeptide such as a *Campylobacter*, *E. coli*, *Flavobacterium*, *Fusobacterium*, *Helicobacter*, *Ilyobacter*, *Neisseria*, *Pseudomonas*, *Salmonella*, or *Ureaplasma* protease.

In one aspect, the polypeptide is a *Bacillus alkalophilus*, *Bacillus amyloliquefaciens*, *Bacillus brevis*, *Bacillus circulans*, *Bacillus clausfi*, *Bacillus coagulans*, *Bacillus firmus*, *Bacillus lautus*, *Bacillus lentus*, *Bacillus licheniformis*, *Bacillus megaterium*, *Bacillus pumilus*, *Bacillus stearothermophilus*, *Bacillus subtilis*, or *Bacillus thuringiensis* protease In one embodiment, the polypeptide is a *Bacillus* sp. protease, e.g., the protease with SEQ ID NO: 2 or the mature polypeptide of SEQ ID NO 6. In one aspect the polypeptide is a *Bacillus idriensis* protease e.g. the protease of SEQ ID NO 4.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The parent may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding a parent may then be obtained by similarly screening a genomic DNA or cDNA library of another microorganism or mixed DNA sample. Once a polynucleotide encoding a parent has been detected with the probe(s), the polynucleotide can be isolated or cloned by utilizing techniques that are known to those of ordinary skill in the art (see, e.g., Sambrook et al., 1989, supra).

Polynucleotides

The present invention also relates to isolated polynucleotides encoding a polypeptide or a catalytic domain of the present invention, as described herein.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *bacillus* or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, or the like. The variants may be constructed on the basis of the polynucleotide presented as the mature polypeptide coding sequence of SEQ ID NO: 1, 3 or 5, e.g., a subsequence thereof, and/or by introduction of nucleotide substitutions that do not result in a change in the amino acid sequence of the polypeptide, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

Signal Peptide and Propeptide

The present invention also relates to a polynucleotide encoding a signal peptide comprising or consisting of amino acids −110 to −84 of SEQ ID NO: 2. The present invention also relates to a polynucleotide encoding a propeptide comprising or consisting of amino acids −83 to −1 of SEQ ID NO: 2. The present invention also relates to a polynucleotide encoding a signal peptide and a propeptide comprising or consisting of amino acids −110 to −1 of SEQ ID NO: 2. The polynucleotides may further comprise a gene encoding a protein, which is operably linked to the signal peptide and/or propeptide. The protein is preferably foreign to the signal peptide and/or propeptide. In one aspect, the polynucleotide encoding the signal peptide is nucleotides 501 to 581 of SEQ ID NO: 1. In another aspect, the polynucleotide encoding the propeptide is nucleotides 582 to 830 of SEQ ID NO: 1. In another aspect, the polynucleotide encoding the signal peptide and the propeptide is nucleotides 501 to 830 of SEQ ID NO: 1.

The present invention further relates to a polynucleotide encoding a signal peptide comprising or consisting of amino acids −103 to −77 of SEQ ID NO: 4. The present invention also relates to a polynucleotide encoding a propeptide comprising or consisting of amino acids −76 to −1 of SEQ ID NO: 4. The present invention also relates to a polynucleotide encoding a signal peptide and a propeptide comprising or consisting of amino acids −103 to −1 of SEQ ID NO: 4. The polynucleotides may further comprise a gene encoding a protein, which is operably linked to the signal peptide and/or propeptide. The protein is preferably foreign to the signal peptide and/or propeptide. In one aspect, the polynucleotide encoding the signal peptide is nucleotides 501 to 581 of SEQ ID NO: 3. In another aspect, the polynucleotide encoding the propeptide is nucleotides 582 to 809 of SEQ ID NO: 3. In another aspect, the polynucleotide encoding the signal peptide and the propeptide is nucleotides 501 to 809 of SEQ ID NO: 3.

The present invention further relates to a polynucleotide encoding a signal peptide comprising or consisting of amino acids −106 to −78 of SEQ ID NO: 6. The present invention also relates to a polynucleotide encoding a propeptide comprising or consisting of amino acids −77 to −1 of SEQ ID NO: 6. The present invention also relates to a polynucleotide encoding a signal peptide and a propeptide comprising or consisting of amino acids −106 to −1 of SEQ ID NO: 6. The polynucleotides may further comprise a gene encoding a protein, which is operably linked to the signal peptide and/or propeptide. The protein is preferably foreign to the signal peptide and/or propeptide. In one aspect, the polynucleotide encoding the signal peptide is nucleotides 501 to 587 of SEQ ID NO: 5. In another aspect, the polynucleotide encoding the propeptide is nucleotides 588 to 818 of SEQ ID NO: 5. In another aspect, the polynucleotide encoding the signal peptide and the propeptide is nucleotides 501 to 818 of SEQ ID NO: 5.

The present invention also relates to nucleic acid constructs, expression vectors and recombinant host cells comprising such polynucleotides.

The present invention also relates to methods of producing a protein, comprising (a) cultivating a recombinant host cell comprising such polynucleotide; and (b) recovering the protein.

The protein may be native or heterologous to a host cell. The term "protein" is not meant herein to refer to a specific length of the encoded product and, therefore, encompasses peptides, oligopeptides, and polypeptides. The term "protein" also encompasses two or more polypeptides combined to form the encoded product. The proteins also include hybrid polypeptides and fused polypeptides.

Preferably, the protein is a hormone, enzyme, receptor or portion thereof, antibody or portion thereof, or reporter. For example, the protein may be a hydrolase, isomerase, ligase, lyase, oxidoreductase, or transferase, e.g., an alpha-galactosidase, alpha-glucosidase, aminopeptidase, amylase, beta-galactosidase, beta-glucosidase, beta-xylosidase, carbohydrase, carboxypeptidase, catalase, cellobiohydrolase, cellulase, chitinase, cutinase, cyclodextrin glycosyltransferase, deoxyribonuclease, endoglucanase, esterase, glucoamylase, invertase, laccase, lipase, mannosidase, mutanase, oxidase, pectinolytic enzyme, peroxidase, phytase, polyphenoloxidase, proteolytic enzyme, ribonuclease, transglutaminase, or xylanase. The gene may be obtained from any prokaryotic, eukaryotic, or other source.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences. Thus, in one aspect, the present invention relates to a nucleic acid construct comprising a polynucleotide encoding polypeptide having at least 85% sequence identity to the mature polypeptide of SEQ ID NO:2; a polypeptide having at least 80% sequence identity to the mature polypeptide of SEQ ID NO:4; or a polypeptide having at least 89% sequence identity to the mature polypeptide of SEQ ID NO: 6, wherein the polynucleotide is operably linked to one or more control sequences that direct the expression of the coding sequence in a suitable host cell under conditions compatible with the control sequences.

A polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Dania (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* anthranilate synthase, *Aspergillus niger* glucoamylase, *Aspergillus niger* alpha-glucosidase, *Aspergillus oryzae* TAKA amylase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence; a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory systems are those that cause expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked with the regulatory sequence.

Expression Vectors

The present invention also relates to recombinant expression vectors comprising a polynucleotide of the present invention, a promoter, and transcriptional and translational stop signals. Thus, in one aspect, the present invention relates to a recombinant expression vector comprising a polynucleotide encoding polypeptide having at least 85% sequence identity to the mature polypeptide of SEQ ID NO:2; a polypeptide having at least 80% sequence identity to the mature polypeptide of SEQ ID NO:4; or a polypeptide having at least 89% sequence identity to the mature polypeptide of SEQ ID NO: 6, wherein the expression vector further comprises a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. Thus, in one aspect, the present invention relates to a recombinant host cell comprising a polynucleotide encoding polypeptide having at least 85% sequence identity to the mature polypeptide of SEQ ID NO:2; a polypeptide having at least 80% sequence identity to the mature polypeptide of SEQ ID NO:4; or a polypeptide having at least 89% sequence identity to the mature polypeptide of SEQ ID NO: 6, wherein the polynucleotide is operably linked to one or more control sequences that direct the expression of the coding sequence in a suitable host cell under conditions compatible with the control sequences. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus,* and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella,* and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* and *Bacillus thuringiensis* cells.

The bacterial host cell may also be any *Streptococcus* cell including, but not limited to, *Streptococcus equisimilis, Streptococcus pyogenes, Streptococcus uberis,* and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus,* and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., In, *Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, Passmore, and Davenport, editors, *Soc. App. Bacteriol. Symposium Series* No. 9, 1980).

The yeast host cell may be a *Candida*, *Hansenula*, *Kluyveromyces*, *Pichia*, *Saccharomyces*, *Schizosaccharomyces*, or *Yarrowia* cell, such as a *Kluyveromyces lactis*, *Saccharomyces carlsbergensis*, *Saccharomyces cerevisiae*, *Saccharomyces diastaticus*, *Saccharomyces douglasii*, *Saccharomyces kluyveri*, *Saccharomyces norbensis*, *Saccharomyces oviformis*, or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell.

For example, the filamentous fungal host cell may be an *Aspergillus awamori*, *Aspergillus foetidus*, *Aspergillus fumigatus*, *Aspergillus japonicus*, *Aspergillus nidulans*, *Aspergillus niger*, *Aspergillus oryzae*, *Bjerkandera adusta*, *Ceriporiopsis aneirina*, *Ceriporiopsis caregiea*, *Ceriporiopsis gilvescens*, *Ceriporiopsis pannocinta*, *Ceriporiopsis rivulosa*, *Ceriporiopsis subrufa*, *Ceriporiopsis subvermispora*, *Chrysosporium inops*, *Chrysosporium keratinophilum*, *Chrysosporium lucknowense*, *Chrysosporium merdarium*, *Chrysosporium pannicola*, *Chrysosporium queenslandicum*, *Chrysosporium tropicum*, *Chrysosporium zonatum*, *Coprinus cinereus*, *Coriolus hirsutus*, *Fusarium bactridioides*, *Fusarium cerealis*, *Fusarium crookwellense*, *Fusarium culmorum*, *Fusarium graminearum*, *Fusarium graminum*, *Fusarium heterosporum*, *Fusarium negundi*, *Fusarium oxysporum*, *Fusarium reticulatum*, *Fusarium roseum*, *Fusarium sambucinum*, *Fusarium sarcochroum*, *Fusarium sporotrichioides*, *Fusarium sulphureum*, *Fusarium torulosum*, *Fusarium trichothecioides*, *Fusarium venenatum*, *Humicola insolens*, *Humicola lanuginosa*, *Mucor miehei*, *Myceliophthora thermophila*, *Neurospora crassa*, *Penicillium purpurogenum*, *Phanerochaete chrysosporium*, *Phlebia radiata*, *Pleurotus eryngii*, *Thielavia terrestris*, *Trametes villosa*, *Trametes versicolor*, *Trichoderma harzianum*, *Trichoderma koningfi*, *Trichoderma longibrachiatum*, *Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing the polypeptides of the present invention, comprising (a) cultivating a cell, which in its wild-type form produces the polypeptide, under conditions conducive for production of the polypeptide; and (b) recovering the polypeptide. Thus, in one aspect, the present invention relates to a method of producing a polypeptide having at least 85% sequence identity to the mature polypeptide of SEQ ID NO:2; a polypeptide having at least 80% sequence identity to the mature polypeptide of SEQ ID NO:4; or a polypeptide having at least 89% sequence identity to the mature polypeptide of SEQ ID NO: 6, wherein the method comprises the steps of (a) cultivating a cell, such as a host cell according to the invention, under conditions conducive for production of the polypeptide; and (b) recovering the polypeptide. In a preferred aspect, the cell is a *Bacillus* cell. In a more preferred aspect, the cell is a *Bacillus* sp. cell. In a most preferred aspect, the cell is selected from *Bacillus* sp-13380, *Bacillus* idriensis or *Bacillus* sp-62451 producing the polypeptides with SEQ ID NO 2, 4 or 6 respectively.

Thus, one embodiment of the invention relates to a method of producing the polypeptide having at least 85% identity to SEQ ID NO: 2, comprising: (a) cultivating a cell, which in its wild-type form produces the polypeptide, under conditions conducive for production of the polypeptide; and (b) recovering the polypeptide.

Another embodiment of the invention relates to a method of producing the polypeptide having at least 80% identity to SEQ ID NO: 4, comprising: (a) cultivating a cell, which in its wild-type form produces the polypeptide, under conditions conducive for production of the polypeptide; and (b) recovering the polypeptide.

A third embodiment of the invention relates to a method of producing the polypeptide having at least 80% identity to SEQ ID NO: 6, comprising: (a) cultivating a cell, which in its wild-type form produces the polypeptide, under conditions conducive for production of the polypeptide; and (b) recovering the polypeptide.

The present invention also relates to methods of producing a polypeptide of the present invention, comprising (a) cultivating a recombinant host cell of the present invention under conditions conducive for production of the polypeptide; and (b) recovering the polypeptide.

Thus, one embodiment of the invention relates to a method of producing the polypeptide having at least 85% identity to SEQ ID NO: 2, comprising:

(a) cultivating a host cell under conditions conducive for production of the polypeptide; and (b) recovering the polypeptide.

Thus, one embodiment of the invention relates to a method of producing the polypeptide having at least 80% identity to SEQ ID NO: 4, comprising:

(a) cultivating a host cell under conditions conducive for production of the polypeptide; and (b) recovering the polypeptide.

Thus, one embodiment of the invention relates to a method of producing the polypeptide having at least 89% identity to SEQ ID NO: 6, comprising:

(a) cultivating a host cell under conditions conducive for production of the polypeptide; and (b) recovering the polypeptide.

The host cell may be a bacterial host cells such a *Bacillus, Streptococcus* or *Streptomyces* cell. The host cell may also be a eukaryote, such as a mammalian, insect, plant, or fungal cell. The host cell may be a fungal cell, which may be a yeast cell. Various suitable host cells are described in the "host cells" section of the present application.

The cell or the host cells are cultivated in a nutrient medium suitable for production of the polypeptide using methods known in the art. For example, the cell may be cultivated by shake flask cultivation, or small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Detergent Compositions

In one aspect, the invention is directed to detergent compositions comprising an enzyme of the present invention in combination with one or more additional cleaning composition components. Thus one embodiment, the present invention relates to a detergent composition comprising an isolated polypeptide having a sequence identity to the mature polypeptide of SEQ ID NO: 2 of at least 85%, at least 86%, at least 87%, at least 88%, at least 89% at least 90%, at least 91%, at least 92%, at least 93%, at least 94%, at least 95%, at least 96%, at least 97%, at least 98%, at least 99%, or 100%, which polypeptide has protease activity.

Another aspect, the present invention relates to a detergent composition comprising an isolated polypeptide having a sequence identity to the mature polypeptide of SEQ ID NO: 4 of at least 80% at least 81% at least 82% at least 83% at least 84%, at least 85%, at least 86%, at least 87%, at least 88%, at least 89% at least 90%, at least 91%, at least 92%, at least 93%, at least 94%, at least 95%, at least 96%, at least 97%, at least 98%, at least 99%, or 100%, which polypeptide has protease activity.

A third aspect, the present invention relates to a detergent composition comprising an isolated polypeptide having a sequence identity to the mature polypeptide of SEQ ID NO: 6 of at least 90%, at least 91%, at least 92%, at least 93%, at least 94%, at least 95%, at least 96%, at least 97%, at least 98%, at least 99%, or 100%, which polypeptide has protease activity.

The choice of additional components is within the skill of the artisan and includes conventional ingredients, including the exemplary non-limiting components set forth below. The choice of components may include, for fabric care, the consideration of the type of fabric to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan and includes conventional ingredients, including the exemplary non-limiting components set forth below.

The choice of components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

The detergent composition may be suitable for laundry of textiles or for hard surface cleaning including dish wash including automated dish wash.

In one embodiment of the present invention, the a polypeptide of the present invention may be added to a detergent composition in an amount corresponding to 0.001-200 mg of protein, such as 0.005-100 mg of protein, preferably 0.01-50 mg of protein, more preferably 0.05-20 mg of protein, even more preferably 0.1-10 mg of protein per liter of wash liquid.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, for example, WO92/19709 and WO92/19708 or the protease according to the invention may be stabilized using peptide aldehydes or ketones such as described in WO 2005/105826 and WO 2009/118375. A polypeptide of the present invention may also be incorporated in the detergent formulations disclosed in WO97/07202, which is hereby incorporated by reference.

Surfactants

The detergent composition may comprise one or more surfactants, which may be anionic and/or cationic and/or non-ionic and/or semi-polar and/or zwitterionic, or a mixture thereof. In a particular embodiment, the detergent composition includes a mixture of one or more non-ionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and includes any conventional surfactant(s) known in the art. Any surfactant known in the art for use in detergents may be utilized.

When included therein the detergent will usually contain from about 1% to about 40% by weight, such as from about 5% to about 30%, including from about 5% to about 15%, or from about 20% to about 25% of an anionic surfactant. Non-limiting examples of anionic surfactants include sulphates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulphonate, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or soap, and combinations thereof.

When included therein the detergent will usually contain from about 1% to about 40% by weight of a cationic surfactant. Non-limiting examples of cationic surfactants include alklydimethylethanolamine quat (ADMEAQ), cetyltrimethylammonium bromide (CTAB), dimethyldistearylammonium chloride (DSDMAC), alkylbenzyldimethylammonium, alkyl quaternary ammonium compounds, alkoxylated quaternary ammonium (AQA) and combinations thereof.

When included therein the detergent will usually contain from about 0.2% to about 40% by weight of a non-ionic surfactant, for example from about 0.5% to about 30%, in particular from about 1% to about 20%, from about 3% to about 10%, such as from about 3% to about 5%, or from about 8% to about 12%. Non-limiting examples of non-ionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamide (PFAM), polyhydroxy alkyl fatty acid amides, or N-acyl N-alkyl derivatives of glucosamine (glucamides, GA, or fatty acid glucamide, FAGA), as well as products available under the trade names SPAN and TWEEN, and combinations thereof.

When included therein the detergent will usually contain from about 1% to about 40% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, fatty acid alkanolamides and ethoxylated fatty acid alkanolamides, and combinations thereof.

When included therein the detergent will usually contain from about 1% to about 40% by weight of a zwitterionic surfactant. Non-limiting examples of zwitterionic surfactants include betaine, alkyldimethylbetaine, and sulfobetaine, and combinations thereof.

Hydrotropes

A hydrotrope is a compound that solubilises hydrophobic compounds in aqueous solutions (or oppositely, polar substances in a non-polar environment). Typically, hydrotropes have both hydrophilic and a hydrophobic character (so-called amphiphilic properties as known from surfactants); however the molecular structure of hydrotropes generally do not favour spontaneous self-aggregation, see e.g. review by Hodgdon and Kaler, 2007, *Current Opinion in Colloid & Interface Science* 12: 121-128. Hydrotropes do not display a critical concentration above which self-aggregation occurs as found for surfactants and lipids forming micelles, lamellar or other well defined meso-phases. Instead, many hydrotropes show a continuous-type aggregation process where the sizes of aggregates grow as concentration increases. However, many hydrotropes alter the phase behaviour, stability, and colloidal properties of systems containing substances of polar and non-polar character, including mixtures of water, oil, surfactants, and polymers. Hydrotropes are classically used across industries from pharma, personal care, food, to technical applications. Use of hydrotropes in detergent compositions allow for example more concentrated formulations of surfactants (as in the process of compacting liquid detergents by removing water) without inducing undesired phenomena such as phase separation or high viscosity.

The detergent may contain 0-5% by weight, such as about 0.5 to about 5%, or about 3% to about 5%, of a hydrotrope. Any hydrotrope known in the art for use in detergents may be utilized. Non-limiting examples of hydrotropes include sodium benzene sulfonate, sodium p-toluene sulfonates (STS), sodium xylene sulfonates (SXS), sodium cumene sulfonates (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

Builders and Co-Builders

The detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in laundry detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), iminodiethanol (DEA), triethanolamine (TEA), and carboxymethylinulin (CMI), and combinations thereof.

The detergent composition may also contain 0-65% by weight, such as about 5% to about 50%, of a detergent co-builder, or a mixture thereof. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2''-nitrilotriacetic acid (NTA), etheylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diylbis(phosphonic acid) (HEDP), ethylenediaminetetrakis(methylene)tetrakis(phosphonic acid) (EDTMPA), diethylenetriaminepentakis(methylene)pentakis(phosphonic acid) (DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl) aspartic acid (SMAS), N-(2-sulfoethyl) aspartic acid (SEAS), N-(2-sulfomethyl) glutamic acid (SMGL), N-(2-sulfoethyl) glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N, N-diacetic acid (SLDA), taurine-N, N-diacetic acid (TUDA) and sulfomethyl-N,N-diacetic acid (SMDA), N-(hydroxyethyl)-ethylenediaminetriacetate (HEDTA), diethanolglycine (DEG), diethylenetriamine penta (Methylene Phosphonic acid) (DTPMP), aminotris(methylenephosphonic acid) (ATMP), and combinations and salts thereof. Further exemplary builders and/or co-builders are described in, e.g., WO 09/102854, U.S. Pat. No. 5,977,053

Bleaching Systems

The detergent may contain 0-10% by weight, such as about 1% to about 5%, of a bleaching system. Any bleaching system known in the art for use in laundry detergents may be utilized. Suitable bleaching system components include bleaching catalysts, photobleaches, bleach activators, sources of hydrogen peroxide such as sodium percarbonate and sodium perborates, preformed peracids and mixtures thereof. Suitable preformed peracids include, but are not limited to, peroxycarboxylic acids and salts, percarbonic acids and salts, perimidic acids and salts, peroxymonosulfuric acids and salts, for example, Oxone (R), and mixtures thereof. Non-limiting examples of bleaching systems include peroxide-based bleaching systems, which may comprise, for example, an inorganic salt, including alkali metal salts such as sodium salts of perborate (usually mono- or tetra-hydrate), percarbonate, persulfate, perphosphate, persilicate salts, in combination with a peracid-forming bleach activator. The term "Bleach activator" as used herein is meant a compound which reacts with peroxygen bleach like hydrogen peroxide to form a peracid. The peracid thus formed constitutes the activated bleach. Suitable bleach activators to be used herein include those belonging to the class of esters amides, imides or anhydrides, Suitable examples are tetraacetyl ethylene diamine (TAED), sodium 3,5,5 trimethyl hexanoyloxybenzene sulfonate, diperoxy dodecanoic acid, 4-(dodecanoyloxy)benzenesulfonate (LOBS), 4-(decanoyloxy)benzenesulfonate, 4-(decanoyloxy)benzoate (DOBS), 4-(3,5,5-trimethylhexanoyloxy) benzenesulfonate (ISONOBS), tetraacetylethylenediamine (TAED) and 4-(nonanoyloxy)benzenesulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like Triacin has the advantage that it is environmental friendly as it eventually degrades into citric acid and alcohol. Furthermore acetyl triethyl citrate and triacetin has a good hydrolytical stability in the product upon storage and it is an efficient bleach activator. Finally ATC provides a good building capacity to the laundry additive. Alternatively, the bleaching system may comprise peroxyacids of, for example, the amide, imide, or sulfone type. The bleaching system may also comprise peracids such as 6-(phthaloylamino)percapronic acid (PAP). The bleaching system may also include a bleach catalyst. In some embodiments the bleach component may be an organic catalyst selected from the group consisting of organic catalysts having the following formulae:

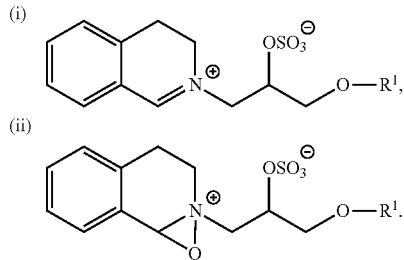

(iii) and mixtures thereof; wherein each $R^1$ is independently a branched alkyl group containing from 9 to 24 carbons or linear alkyl group containing from 11 to 24 carbons, preferably each $R^1$ is independently a branched alkyl group containing from 9 to 18 carbons or linear alkyl group containing from 11 to 18 carbons, more preferably each $R^1$ is independently selected from the group consisting of 2-propylheptyl, 2-butyloctyl, 2-pentylnonyl, 2-hexyldecyl, n-dodecyl, n-tetradecyl, n-hexadecyl, n-octadecyl, iso-nonyl, iso-decyl, iso-tridecyl and iso-pentadecyl. Other exemplary bleaching systems are described, e.g., in WO2007/087258, WO2007/087244, WO2007/087259, WO2007/087242. Suitable photobleaches may for example be sulfonated zinc phthalocyanine Polymers The detergent may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or antifoaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of polyethylene terephthalate and polyoxyethene terephthalate (PET-POET), PVP, poly(vinylimidazole) (PVI), poly(vinylpyridin-N-oxide) (PVPO or PVPNO) and polyvinylpyrrolidone-vinylimidazole (PVPVI). Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated.

Fabric Hueing Agents

The detergent compositions of the present invention may also include fabric hueing agents such as dyes or pigments which when formulated in detergent compositions can deposit onto a fabric when said fabric is contacted with a wash liquid comprising said detergent compositions thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof, for example as described in WO2005/03274, WO2005/03275, WO2005/03276 and EP1876226 (hereby incorporated by reference). The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Suitable hueing agents are also disclosed in, e.g., WO 2007/087257, WO2007/087243.

Additional Enzymes

The detergent additive as well as the detergent composition may comprise one or more additional enzymes such as a protease, lipase, cutinase, an amylase, carbohydrase, cellulase, pectinase, mannanase, arabinase, galactanase, xylanase, oxidase, e.g., a laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts.

Thus, in one embodiment, the detergent composition comprises one or more additional enzymes, wherein the additional enzymes is selected from the group consisting of
i) a protease comprising one or more modifications in the following positions: 32, 33, 48-54, 58-62, 94-107, 116, 123-133, 150, 152-156, 158-161, 164, 169, 175-186, 197, 198, 203-216 as compared with the protease in SEQ ID NO:17;
ii) a lipase comprising one or more modifications in the following positions: 1-5, 27, 33, 38, 57, 91, 94, 96, 97, 111, 163, 210, 225, 231, 233, 249, and 254-256 as compared with the lipase in SEQ ID NO:18;
iii) an alpha-amylase comprising one or more modifications in the following positions: 9, 118, 149, 182, 186, 195, 202, 257, 295, 299, R320, 323, 339, 345, and 458 as compared with the alpha-amylase in SEQ ID NO:19;
iv) an alpha-amylase comprising one or more modifications in the following positions: 140, 195, 206, 243, 260 and 476 as compared with the alpha-amylase in SEQ ID NO:20;
v) an alpha-amylase comprising one or more modifications in the following positions: 180, 181, 243, and 475 as compared with the alpha-amylase in SEQ ID NO:21;
vi) an alpha-amylase comprising one or more modifications in the following positions: 178, 179, 187, 203, 458, 459, 460, and 476 as compared with the alpha-amylase in SEQ ID NO:22;
vii) an alpha-amylase comprising a modifications in the following position: 202 as compared with the alpha-amylase in SEQ ID NO:23;
viii) an alpha-amylase comprising one or more modifications in the following positions: 405, 421, 422, and 428 as compared with the alpha-amylase in SEQ ID NO:24; and/or
ix) an alpha-amylase according to SEQ ID NO:25.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and WO99/001544.

Other cellulases are endo-beta-1, 4-glucanase enzyme having a sequence of at least 97% identity to the amino acid sequence of position 1 to position 773 of SEQ ID NO: 2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S) Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, and Puradax HA™ (Genencor International Inc.), and KAC-500(B)™ (Kao Corporation).

Proteases suitable proteases to be used with the protease of the invention include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B. amyloliquefaciens, Bacillus pumilus* and *Bacillus gibsonii* described in; U.S. Pat. No. 7,262,042 and WO09/021867, and subtilisin lentus, subtilisin Novo, subtilisin Carlsberg, *Bacillus licheniformis*, subtilisin BPN', subtilisin 309, subtilisin 147 and subtilisin 168 described in WO89/06279 and protease PD138 described in (WO93/18140). Other useful proteases may be those described in WO92/175177, WO01/016285, WO02/026024 and WO02/016547. Examples of trypsin-like proteases are trypsin (e.g. of porcine or bovine origin) and the *Fusarium* protease described in WO89/06270, WO94/25583 and WO05/040372, and the chymotrypsin proteases derived from *Cellulomonas* described in WO05/052161 and WO05/052146.

A further preferred protease is the alkaline protease from *Bacillus lentus* DSM 5483, as described for example in WO95/23221, and variants thereof which are described in WO92/21760, WO95/23221, EP1921147 and EP1921148.

Examples of metalloproteases are the neutral metalloprotease as described in WO07/044993 (Genencor Int.) such as those derived from *Bacillus amyloliquefaciens*.

Examples of useful proteases are the variants described in: WO92/19729, WO96/034946, WO98/20115, WO98/20116, WO99/011768, WO01/44452, WO03/006602, WO04/03186, WO04/041979, WO07/006305, WO11/036263, WO11/036264, especially the variants with substitutions in one or more of the following positions: 3, 4, 9, 15, 27, 36, 57, 61, 68, 76, 87, 95, 96, 97, 98, 99, 100, 101, 102, 103, 104, 106, 118, 120, 123, 128, 129, 130, 160, 167, 170, 194, 195, 199, 205, 206, 217, 218, 222, 224, 232, 235, 236, 245, 248, 252 and 274 using the BPN' numbering. More preferred the subtilase variants may comprise the mutations: S3T, V4I, S9R, A15T, K27R, *36D, G61E,D, V68A, N76D, N87S,R, *97E, A98S, S99G,D,A, S99AD, S101G,M,R S103A, V104I,Y,N, S106A, G118V,R, H120D,N, N123S, S128L, P129Q, S130A, G160D, Y167A, R170S, A194P, G195E, V199M, V205I, L217D, N218D, M222S, A232V, K235L, Q236H, Q245R, N252K, T274A (using BPN' numbering).

Suitable commercially available protease enzymes include those sold under the trade names ALCALASE®, DURALASE™, DURAZYME™, RELASE®, RELASE® Ultra, SAVINASE®, SAVINASE® Ultra, PRIMASE®, POLARZYME®, KANNASE®, LIQUANASE®, LIQUANASE® Ultra, OVOZYME®, CORONASE®, CORONASE® Ultra, NEUTRASE®, EVERLASE® AND ESPERASE® (Novozymes A/S), those sold under the tradename MAXATASE®, MAXACAL®, MAXAPEM®, PURAFECT®, PURAFECT PRIME®, PREFERENZ™, PURAFECT MA®, PURAFECT OX®, PURAFECT OXP®, PURAMAX®, PROPERASE®, EFFECTENZ™, FN2®, FN3®, FN4®, EXCELLASE®, ULTIMASE®, OPTICLEAN® AND OPTIMASE® (Danisco/DuPont), AXPEM™ (Gist-Brocases N.V.), BLAP (sequence shown in FIG. 29 of U.S. Pat. No. 5,352,604) and variants thereof (Henkel AG) and KAP (*Bacillus alkalophilus* subtilisin) from Kao.

Lipases and Cutinases

Suitable lipases and cutinases include those of bacterial or fungal origin. Chemically modified or protein engineered mutant enzymes are included. Examples include lipase from *Thermomyces*, e.g. from T. *lanuginosus* (previously named *Humicola lanuginosa*) as described in EP258068 and EP305216, cutinase from *Humicola*, e.g. *H. insolens* (WO96/13580), lipase from strains of *Pseudomonas* (some of these now renamed to *Burkholderia*), e.g. *P. alcaligenes* or *P. pseudoalcaligenes* (EP218272), *P. cepacia* (EP331376), P. sp. strain SD705 (WO95/06720 & WO96/27002), *P. wisconsinensis* (WO96/12012), GDSL-type *Streptomyces* lipases (WO10/065455), cutinase from *Magnaporthe grisea* (WO10/107560), cutinase from *Pseudomonas mendocina* (U.S. Pat. No. 5,389,536), lipase from *Thermobifida fusca* (WO11/084412), *Geobacillus stearothermophilus* lipase (WO11/084417), lipase from *Bacillus subtilis* (WO11/084599), and lipase from *Streptomyces griseus* (WO11/150157) and *S. pristinaespiralis* (WO12/137147).

Other examples are lipase variants such as those described in EP407225, WO92/05249, WO94/01541, WO94/25578, WO95/14783, WO95/30744, WO95/35381, WO95/22615, WO96/00292, WO97/04079, WO97/07202, WO00/34450, WO00/60063, WO01/92502, WO07/87508 and WO09/109500.

Preferred commercial lipase products include LIPOLASE™, LIPEX™, LIPOLEX™ and LIPOCLEAN™ (Novozymes A/S), LUMAFAST (originally from Genencor) and LIPOMAX (originally from Gist-Brocades).

Still other examples are lipases sometimes referred to as acyl transferases or perhydrolases, e.g. acyltransferases with homology to *Candida antarctica* lipase A (WO10/111143), acyltransferase from *Mycobacterium smegmatis* (WO05/56782), perhydrolases from the CE 7 family (WO09/67279), and variants of the *M. smegmatis* perhydrolase in particular the S54V variant used in the commercial product Gentle Power Bleach from Huntsman Textile Effects Pte Ltd (WO10/100028).

Amylases

Suitable amylases which can be used together with the protease of the invention may be an alpha-amylase or a glucoamylase and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 95/10603 or variants having 90% sequence identity to SEQ ID NO: 3 thereof. Preferred variants are described in WO 94/02597, WO 94/18314, WO 97/43424 and SEQ ID NO: 4 of WO 99/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 02/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;
H156Y+A181T+N190F+A209V+Q264S; or
G48A+T49I+G107A+H156Y+A181T+N190F+I201F+A209V+Q264S.

Further amylases which are suitable are amylases having SEQ ID NO: 6 in WO 99/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 96/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 08/153815, SEQ ID NO: 10 in WO 01/66712 or variants thereof having 90% sequence identity to SEQ ID NO: 2 of WO 08/153815 or 90% sequence identity to SEQ ID NO: 10 in WO 01/66712. Preferred variants of SEQ ID NO: 10 in WO 01/66712 are those having a substitution, a deletion or an insertion in one of more of the following positions: 176, 177, 178, 179, 190, 201, 207, 211 and 264.

Further suitable amylases are amylases having SEQ ID NO: 2 of WO 09/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:
N128C+K178L+T182G+Y305R+G475K;
N128C+K178L+T182G+F202Y+Y305R+D319T+G475K;
S125A+N128C+K178L+T182G+Y305R+G475K; or
S125A+N128C+T131I+T165I+K178L+T182G+Y305R+G475K wherein the variants are C-terminally truncated and optionally further comprises a substitution at position 243 and/or a deletion at position 180 and/or position 181.

Other suitable amylases are the alpha-amylase having SEQ ID NO: 12 in WO01/66712 or a variant having at least 90% sequence identity to SEQ ID NO: 12. Preferred amylase variants are those having a substitution, a deletion or an insertion in one of more of the following positions of SEQ ID NO: 12 in WO01/66712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO2011/098531, WO2013/001078 and WO2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase and Preferenz S100 (from Genencor International Inc./DuPont).

Peroxidases/Oxidases

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257.

Commercially available peroxidases include Guardzyme™ (Novozymes A/S).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, for example, as a granulate, liquid, slurry, etc. Preferred detergent additive formulations are granulates, in particular non-dusting granulates, liquids, in particular stabilized liquids, or slurries.

Non-dusting granulates may be produced, e.g. as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238,216.

Adjunct Materials

Any detergent components known in the art for use in laundry detergents may also be utilized. Other optional detergent components include anti-corrosion agents, anti-shrink agents, anti-soil redeposition agents, anti-wrinkling agents, bactericides, binders, corrosion inhibitors, disintegrants/disintegration agents, dyes, enzyme stabilizers (including boric acid, borates, CMC, and/or polyols such as propylene glycol), fabric conditioners including clays, fillers/processing aids, fluorescent whitening agents/optical brighteners, foam boosters, foam (suds) regulators, perfumes, soil-suspending agents, softeners, suds suppressors, tarnish inhibitors, and wicking agents, either alone or in combination. Any ingredient known in the art for use in laundry detergents may be utilized. The choice of such ingredients is well within the skill of the artisan.

Dispersants

The detergent compositions of the present invention can also contain dispersants. In particular powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker, Inc.

Dye Transfer Inhibiting Agents

The detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

Fluorescent Whitening Agent

The detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulphonic acid derivatives, diarylpyrazoline derivatives and bisphenyl-distyryl derivatives. Examples of the diaminostilbene-sulphonic acid derivative type of fluorescent whitening agents include the sodium salts of: 4,4'-bis-(2-diethanolamino-4-anilino-s-triazin-6-ylamino) stilbene-2,2'-disulphonate; 4,4'-bis-(2,4-dianilino-s-triazin-6-ylamino) stilbene-2,2'-disulphonate; 4,4'-bis-(2-anilino-4(N-methyl-N-2-hydroxy-ethylamino)-s-triazin-6-ylamino) stilbene-2,2'-disulphonate, 4,4'-bis-(4-phenyl-2,1,3-triazol-2-yl)stilbene-2,2'-disulphonate; 4,4'-bis-(2-anilino-4(1-methyl-2-hydroxy-ethylamino)-s-triazin-6-ylamino) stilbene-2,2'-disulphonate and 2-(stilbyl-4"-naptho-1,2':4,5)-1,2,3-trizole-2"-sulphonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4 anilino-s-triazin-6-ylamino) stilbene disulphonate. Tinopal CBS is the disodium salt of 2,2'-bis-(phenyl-styryl) disulphonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins.

Suitable fluorescent brightener levels include lower levels of from about 0.01, from 0.05, from about 0.1 or even from about 0.2 wt % to upper levels of 0.5 or even 0.75 wt %.

Soil Release Polymers

The detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, polyester polyamides see for example Chapter 7 in Powdered Detergents, Surfactant science series volume 71, Marcel Dekker, Inc. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure as described in detail in WO 2009/087523 (hereby incorporated by reference). Furthermore random graft co-polymers are suitable soil release polymers Suitable graft co-polymers are described in more detail in WO 2007/138054, WO 2006/108856 and WO 2006/113314 (hereby incorporated by reference). Other soil release polymers are substituted polysaccharide structures especially substituted cellulosic structures such as modified cellulose deriviatives such as those described in EP 1867808 or WO 2003/040279 (both are hereby incorporated by reference). Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

Anti-Redeposition Agents

The detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

Other suitable adjunct materials include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents.

Formulation of Detergent Products

The detergent composition of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Detergent formulation forms: Layers (same or different phases), Pouches, various forms for Machine dosing unit.

Pouches may be configured as single or multicompartments. It may be of any form, shape and material which is suitable for hold the composition, e.g. without allowing the release of the composition from the pouch prior to water contact. The pouch is made from water soluble film which encloses an inner volume. Said inner volume may be divided into compartments of the pouch. Preferred films are polymeric materials preferably polymers which are formed into a film or sheet. Preferred polymers, copolymers or derivatives thereof are selected polyacrylates, and water soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxyprpyl methyl cellulose (HPMC). Preferably the level of polymer in the film for example PVA is at least about 60%. Preferred average molecular weight will typically be about 20,000 to about 150,000. Films can also be of blend compositions comprising hydrolytically degradable and water soluble polymer blends such as polyactide and polyvinyl alcohol (known under the Trade reference M8630 as sold by Chris Craft In. Prod. Of Gary, Ind., US) plus plasticisers like glycerol, ethylene glycerol, Propylene glycol, sorbitol and mixtures thereof. The pouches can comprise a solid laundry cleaning composition or part components and/or a liquid cleaning composition or part components separated by the water soluble film. The compartment for liquid components can be different in composition than compartments containing solids. Ref: (US2009/0011970 A1).

Detergent ingredients may be separated physically from each other by compartments in water dissolvable pouches or in different layers of tablets. Thereby negative storage interaction between components may be avoided. Different dissolution profiles of each of the compartments may also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Laundry Soap Bars

The enzymes of the invention may be added to laundry soap bars and used for hand washing laundry, fabrics and/or textiles. The term "laundry soap bar" as used herein includes laundry bars, soap bars, combo bars, syndet bars and detergent bars. The types of bar usually differ in the type of surfactant they contain, and the term laundry soap bar includes those containing soaps from fatty acids and/or synthetic soaps. The laundry soap bar has a physical form which is solid and not a liquid, gel or a powder at room temperature. The term solid is defined as a physical form which does not significantly change over time, i.e. if a solid object (e.g. laundry soap bar) is placed inside a container, the solid object does not change to fill the container it is placed in. The bar is a solid typically in bar form but can be in other solid shapes such as round or oval.

The laundry soap bar may contain one or more additional enzymes, protease inhibitors such as peptide aldehydes (or hydrosulfite adduct or hemiacetal adduct), boric acid, borate, borax and/or phenylboronic acid derivatives such as 4-formylphenylboronic acid, one or more soaps or synthetic surfactants, polyols such as glycerine, pH controlling compounds such as fatty acids, citric acid, acetic acid and/or formic acid, and/or a salt of a monovalent cation and an organic anion wherein the monovalent cation may be for example $Na^+$, $K^+$ or $NH_4^+$ and the organic anion may be for example formate, acetate, citrate or lactate such that the salt of a monovalent cation and an organic anion may be, for example, sodium formate.

The laundry soap bar may also contain complexing agents like EDTA and HEDP, perfumes and/or different type of fillers, surfactants e.g. anionic synthetic surfactants, builders, polymeric soil release agents, detergent chelators, stabilizing agents, fillers, dyes, colorants, dye transfer inhibitors, alkoxylated polycarbonates, suds suppressers, structurants, binders, leaching agents, bleaching activators, clay soil removal agents, anti-redeposition agents, polymeric dispersing agents, brighteners, fabric softeners, perfumes and/or other compounds known in the art.

The laundry soap bar may be processed in conventional laundry soap bar making equipment such as but not limited to: mixers, plodders, e.g. a two stage vacuum plodder, extruders, cutters, logo-stampers, cooling tunnels and wrappers. The invention is not limited to preparing the laundry soap bars by any single method. The premix of the invention may be added to the soap at different stages of the process. For example, the premix containing a soap, an enzyme, optionally one or more additional enzymes, a protease inhibitor, and a salt of a monovalent cation and an organic anion may be prepared and the mixture is then plodded. The enzyme and optional additional enzymes may be added at the same time as the protease inhibitor for example in liquid form. Besides the mixing step and the plodding step, the process may further comprise the steps of milling, extruding, cutting, stamping, cooling and/or wrapping.

Granular Detergent Formulations

A granular detergent may be formulated as described in WO09/092699, EP1705241, EP1382668, WO07/001262, U.S. Pat. No. 6,472,364, WO04/074419 or WO09/102854. Other useful detergent formulations are described in WO09/124162, WO09/124163, WO09/117340, WO09/117341, WO09/117342, WO09/072069, WO09/063355, WO09/132870, WO09/121757, WO09/112296, WO09/112298, WO09/103822, WO09/087033, WO09/050026, WO09/047125, WO09/047126, WO09/047127, WO09/047128, WO09/021784, WO09/010375, WO09/000605, WO09/122125, WO09/095645, WO09/040544, WO09/040545, WO09/024780, WO09/004295, WO09/004294, WO09/121725, WO09/115391, WO09/115392, WO09/074398, WO09/074403, WO09/068501, WO09/065770, WO09/021813, WO09/030632, and WO09/015951. WO2011025615, WO2011016958, WO2011005803, WO2011005623, WO2011005730, WO2011005844, WO2011005904, WO2011005630, WO2011005830, WO2011005912, WO2011005905, WO2011005910, WO2011005813, WO2010135238, WO2010120863, WO2010108002, WO2010111365, WO2010108000, WO2010107635, WO2010090915, WO2010033976, WO2010033746, WO2010033747, WO2010033897, WO2010033979, WO2010030540, WO2010030541, WO2010030539, WO2010024467, WO2010024469, WO2010024470, WO2010025161, WO2010014395, WO2010044905, WO2010145887, WO2010142503, WO2010122051, WO2010102861, WO2010099997, WO2010084039, WO2010076292, WO2010069742, WO2010069718, WO2010069957, WO2010057784, WO2010054986, WO2010018043, WO2010003783, WO2010003792, WO2011023716, WO2010142539, WO2010118959, WO2010115813, WO2010105942, WO2010105961, WO2010105962, WO2010094356, WO2010084203, WO2010078979, WO2010072456, WO2010069905, WO2010076165, WO2010072603, WO2010066486, WO2010066631, WO2010066632, WO2010063689, WO2010060821, WO2010049187, WO2010031607, WO2010000636.

Uses

The present invention is directed to methods for using the polypeptides having protease activity, or compositions thereof. The invention may be used in compositions thereof in the laundering of textile and fabrics, such as house hold laundry washing and industrial laundry washing. The invention is directed to methods for using the compositions thereof in hard surface cleaning such as automated dish washing (ADW), car wash and cleaning of industrial surfaces.

Use of Proteases of the Invention in Detergent Compositions and Cleaning Processes The soils and stains that are important for detergent formulators are composed of many different substances, and a range of different enzymes, all with different substrate specificities have been developed for use in detergents both in relation to laundry and hard surface cleaning, such as dishwashing. These enzymes are considered to provide an enzyme detergency benefit, since they specifically improve stain removal in the cleaning process they are applied in as compared to the same process without enzymes. Stain removing enzymes that are known in the art include enzymes such as carbohydrases, amylases, proteases, lipases, cellulases, hemicellulases, xylanases, cutinases, and pectinase.

In one aspect, the present invention relates to the use of an isolated polypeptide having a sequence identity to the mature polypeptide of SEQ ID NO: 2 of at least 85%, at least 86%, at least 87%, at least 88%, at least 89% at least 90%, at least 91%, at least 92%, at least 93%, at least 94%, at least 95%, at least 96%, at least 97%, at least 98%, at least 99%, or 100% in detergent compositions and cleaning processes, such as laundry and hard surface cleaning.

In one aspect, the present invention relates to the use of an isolated polypeptide having a sequence identity to the mature polypeptide of SEQ ID NO: 4 of at least 80% at least 81% at least 82% at least 83% at least 84%, at least 85%, at least 86%, at least 87%, at least 88%, at least 89% at least 90%, at least 91%, at least 92%, at least 93%, at least 94%, at least 95%, at least 96%, at least 97%, at least 98%, at least 99%, or 100% in detergent compositions and cleaning processes, such as laundry and hard surface cleaning.

In one aspect, the present invention relates to the use of an isolated polypeptide having a sequence identity to the mature polypeptide of SEQ ID NO: 6 of at least 90%, at least 91%, at least 92%, at least 93%, at least 94%, at least 95%, at least 96%, at least 97%, at least 98%, at least 99%, or 100% in detergent compositions and cleaning processes, such as laundry and hard surface cleaning.

In another aspect, the present invention relates to the use of protease of the invention in detergent compositions and cleaning processes, such as laundry and hard surface cleaning. Thus, in one aspect, the present invention demonstrates the detergency effect of the protease of the invention on various stains and under various conditions. In a particular embodiment the detergent composition according to the invention and the use in cleaning process relates to the use of a protease of the invention together with at least one of the above mentioned stain removal enzymes.

In a preferred embodiment of the present invention, the protease of the invention may be combined with additional enzymes these additional enzymes are described in details in the section "other enzymes"; preferably the protease of the invention is combined with at least two enzymes, more preferred at least three, four or five enzymes. Preferably, the enzymes have different substrate specificity, e.g., carbolytic activity, proteolytic activity, amylolytic activity, lipolytic activity, hemicellulytic activity or pectolytic activity. The enzyme combination may for example be a protease of the invention with another stain removing enzyme, e.g., a protease of the invention and an amylase, a protease of the invention and a cellulase, a protease of the invention and a hemicellulase, a protease of the invention and a lipase, a protease of the invention and a cutinase, a protease of the invention and a pectinase; or a protease of the invention and an anti-redeposition enzyme, particularly preferred a protease of the invention and an amylase. More preferably, the protease of the invention is combined with at least two other stain removing enzymes, e.g., a protease of the invention, a lipase and an amylase; or a protease of the invention, an amylase and a pectinase; or a protease of the invention, an amylase and a cutinase; or a protease of the invention, an amylase and a cellulase; or a protease of the invention, an amylase and a hemicellulase; or a protease of the invention, a lipase and a pectinase; or a protease of the invention, a lipase and a cutinase; or a protease of the invention, a lipase and a cellulase; or a protease of the invention, a lipase and a hemicellulase. Even more preferably, a protease of the invention may be combined with at least three other stain removing enzymes, e.g., a protease of the invention, an amylase, a lipase and a pectinase; or a protease of the invention, an amylase, a lipase and a cutinase; or a protease of the invention, an amylase, a lipase and a cellulase; or a protease of the invention, an amylase, a lipase and a hemicellulase, preferably a protease of the invention, a lipase, an amylase and a cellulase. A protease of the invention may be combined with any of the enzymes selected from the non-exhaustive list comprising: carbohydrases, such as an amylase, a hemicellulase, a pectinase, a cellulase, a xanthanase or a pullulanase, a peptidase, other proteases or a lipase.

In another embodiment of the present invention, a protease of the invention may be combined with one or more metalloproteases, such as a M4 Metalloprotease, including Neutrase™ or Thermolysin. Such combinations may further comprise combinations of the other detergent enzymes as outlined above.

The cleaning process or the textile care process may for example be a laundry process, a dishwashing process or cleaning of hard surfaces such as bathroom tiles, floors, table tops, drains, sinks and washbasins. Laundry processes may for example be household laundering, but it may also be industrial laundering. Furthermore, the invention relates to a process for laundering of fabrics and/or garments where the process comprises treating fabrics with a washing solution containing a detergent composition, and at least one protease of the invention. The cleaning process or a textile care process may for example be carried out in a machine washing process or in a manual washing process. The washing solution can for example be an aqueous washing solution containing a detergent composition.

The fabrics and/or garments subjected to a washing, cleaning or textile care process of the present invention may be conventional washable laundry, for example household laundry. Preferably, the major part of the laundry is garments and fabrics, including knits, woven, denims, non-woven, felts, yarns, and towelling. The fabrics may be cellulose based such as natural cellulosics, including cotton, flax, linen, jute, ramie, sisal or coir or manmade cellulosics (e.g., originating from wood pulp) including viscose/rayon, ramie, cellulose acetate fibers (tricell), lyocell or blends thereof. The fabrics may also be non-cellulose based such as natural polyamides including wool, camel, cashmere, mohair, rabbit and silk or synthetic polymer such as nylon, aramid, polyester, acrylic, polypropylene and spandex/elastane, or blends thereof as well as blend of cellulose based and non-cellulose based fibers. Examples of blends are blends of cotton and/or rayon/viscose with one or more companion material such as wool, synthetic fibers (e.g., polyamide fibers, acrylic fibers, polyester fibers, polyvinyl alcohol fibers, polyvinyl chloride fibers, polyurethane fibers, polyurea fibers, aramid fibers), and cellulose-containing fibers (e.g., rayon/viscose, ramie, flax, linen, jute, cellulose acetate fibers, lyocell).

The last few years there has been an increasing interest in replacing components in detergents, which is derived from petrochemicals with renewable biological components such as enzymes and polypeptides without compromising the wash performance. When the components of detergent compositions change new enzyme activities or new enzymes having alternative and/or improved properties compared to the common used detergent enzymes such as proteases, lipases and amylases is needed to achieve a similar or improved wash performance when compared to the traditional detergent compositions.

A protease of the invention is usable in proteinaceous stain removing processes. The proteinaceous stains may be stains such as food stains, or e.g., baby food, sebum, cocoa, egg, blood, milk, ink, grass, or a combination hereof.

Typical detergent compositions includes various components in addition to the enzymes, these components have different effects, some components like the surfactants lower the surface tension in the detergent, which allows the stain being cleaned to be lifted and dispersed and then washed away, other components like bleach systems removes discolour often by oxidation and many bleaches also have strong bactericidal properties, and are used for disinfecting and sterilizing. Yet other components like builder and chelator softens, e.g., the wash water by removing the metal ions form the liquid.

In a particular embodiment, the invention relates to the use of a composition comprising a protease of the invention, wherein said enzyme composition further comprises at least one or more of the following a surfactant, a builder, a chelator or chelating agent, bleach system or bleach component in laundry or dish wash.

Thus, in one embodiment, the invention relates to the use of a composition comprising a polypeptide having at least 85% sequence identity to the mature polypeptide of SEQ ID NO: 2; a polypeptide having at least 80% sequence identity to the mature polypeptide of SEQ ID NO:4; or a polypeptide having at least 89% sequence identity to the mature polypeptide of SEQ ID NO:6, wherein the composition further comprises at least one or more of the following; a surfactant, a builder, a chelator or chelating agent, bleach system or bleach component in laundry or dish wash.

In a preferred embodiment of the invention, the amount of a surfactant, a builder, a chelator or chelating agent, bleach system and/or bleach component are reduced compared to amount of surfactant, builder, chelator or chelating agent, bleach system and/or bleach component used without the added protease of the invention. Preferably the at least one component which is a surfactant, a builder, a chelator or chelating agent, bleach system and/or bleach component is present in an amount that is 1% less, such as 2% less, such as 3% less, such as 4% less, such as 5% less, such as 6% less, such as 7% less, such as 8% less, such as 9% less, such as 10% less, such as 15% less, such as 20% less, such as 25% less, such as 30% less, such as 35% less, such as 40% less, such as 45% less, such as 50% less than the amount of the component in the system without the addition of protease of the invention, such as a conventional amount of such component. In one embodiment, the protease of the invention is used in detergent compositions wherein said composition is free of at least one component which is a surfactant, a builder, a chelator or chelating agent, bleach system or bleach component and/or polymer.

Washing Method

The detergent compositions comprising a protease of the present invention are ideally suited for use in laundry applications. Accordingly, the present invention includes a method for laundering a fabric. The method comprises the steps of contacting a fabric to be laundered with a cleaning laundry solution comprising the detergent composition according to the invention. The fabric may comprise any fabric capable of being laundered in normal consumer use conditions. The solution preferably has a pH of from about 5.5 to about 8. The compositions may be employed at concentrations of from about 100 ppm, preferably 500 ppm to about 15,000 ppm in solution. The water temperatures typically range from about 5° C. to about 90° C., including about 10° C., about 15° C., about 20° C., about 25° C., about 30° C., about 35° C., about 40° C., about 45° C., about 50° C., about 55° C., about 60° C., about 65° C., about 70° C., about 75° C., about 80° C., about 85° C. and about 90° C. The water to fabric ratio is typically from about 1:1 to about 30:1.

In particular embodiments, the washing method is conducted at a pH of from about 5.0 to about 11.5, or in alternative embodiments, even from about 6 to about 10.5, such as about 5 to about 11, about 5 to about 10, about 5 to about 9, about 5 to about 8, about 5 to about 7, about 5.5 to about 11, about 5.5 to about 10, about 5.5 to about 9, about 5.5 to about 8, about 5.5. to about 7, about 6 to about 11, about 6 to about 10, about 6 to about 9, about 6 to about 8, about 6 to about 7, about 6.5 to about 11, about 6.5 to about 10, about 6.5 to about 9, about 6.5 to about 8, about 6.5 to about 7, about 7 to about 11, about 7 to about 10, about 7 to about 9, or about 7 to about 8, preferably about 5.5 to about 9, and more preferably about 6 to about 8.

In particular embodiments, the washing method is conducted at a degree of hardness of from about 0° dH to about 30° dH, such as about 1° dH, about 2° dH, about 3° dH, about 4° dH, about 5° dH, about 6° dH, about 7° dH, about 8° dH, about 9° dH, about 10° dH, about 11° dH, about 12° dH, about 13° dH, about 14° dH, about 15° dH, about 16° dH, about 17° dH, about 18° dH, about 19° dH, about 20° dH, about 21° dH, about 22° dH, about 23° dH, about 24° dH, about 25° dH, about 26° dH, about 27° dH, about 28° dH, about 29° dH, about 30° dH. Under typical European wash conditions, the degree of hardness is about 15° dH, under typical US wash conditions about 6° dH, and under typical Asian wash conditions, about 3° dH.

The present invention relates to a method of cleaning a fabric, a dishware or hard surface with a detergent composition comprising a protease of the invention.

A preferred embodiment concerns a method of cleaning, said method comprising the steps of: contacting an object with a cleaning composition comprising a protease of the invention under conditions suitable for cleaning said object. In a preferred embodiment the cleaning composition is a detergent composition and the process is a laundry or a dish wash process.

Still another embodiment relates to a method for removing stains from fabric which comprises contacting said a fabric with a composition comprising a protease of the invention under conditions suitable for cleaning said object.

In a preferred embodiment, the compositions for use in the methods above further comprises at least one additional enzyme as set forth in the "other enzymes" section above, such as an enzyme selected from the group consisting of carbohydrases, amylases, peptidases, proteases, lipases, cellulase, xylanases or cutinases or a combination hereof. In yet another preferred embodiment the compositions comprises a reduced amount of at least one or more of the following components a surfactant, a builder, a chelator or chelating agent, bleach system or bleach component or a polymer.

EXAMPLES

Example 1: Expression and Purification

Isolation, Genome Sequencing and Identification of the Encoding Genes from, *Bacillus* sp.-1 (SEQ ID NO 1), *Bacillus idriensis* (SEQ ID NO 3) and *Bacillus* sp.-2 (SEQ ID NO 5).

Three bacterial strains from the genus *Bacillus* were isolated from various sources under different physiological conditions and the species identified by sequencing of the 16S ribosomal subunit genes as listed in Table 1.

TABLE 1

| Strain | Source type | Location | Medium | Temperature |
|---|---|---|---|---|
| *Bacillus* sp-1 (SEQ ID NO 1) | Environmental sample | Japan | TY medium pH 9 | 30 C. |
| *Bacillus idriensis* (SEQ ID NO 3) | Mud | Antarctica | Marine 2216 medium + 1% skimmilk | 10 C. |
| *Bacillus* sp-2 (SEQ ID NO 5) | Environmental sample | United states | Minimal medium + 1% skim milk pH 10 | 30 C. |

Chromosomal DNA from the bacterial strains was isolated by using the QIAamp DNA Blood Mini Kit" (Qiagen, Hilden, Germany). 2 ug of chromosomal DNA was sent for genome sequencing at FASTERIS SA, Switzerland. The genomes were sequenced by Illumina Sequencing. The resulting genome sequences were analyzed and three proteases were identified by comparison to the protease TY145 (SEQ ID NO: 10) by searching using the BLAST program. The DNA sequence of the identified genes encoding the polypeptides of the invention is included in the sequence listing as SEQ ID NO: 2, SEQ ID NO: 4 and SEQ ID NO: 6.

Cloning and Expression of Three Proteases from *Bacillus* sp.-1, *Bacillus idriensis* and *Bacillus* sp.-2 in *Bacillus subtilis* Expression Host.

A linear integration vector-system was used for the expression cloning of the proteases from *Bacillus* sp.-1 (SEQ ID NO: 2), *Bacillus idriensis* (SEQ ID NO: 4) and *Bacillus* sp.-2(SEQ ID NO: 6). The linear integration construct was a FOR fusion product made by fusion of the gene between two *Bacillus subtilis* homologous chromosomal regions along with strong promoters and a chloramphenicol resistance marker. The fusion was made by SOE PCR (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68). The SOE PCR method is also described in patent application WO 2003/095658. The gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The gene coding for chloramphenicol acetyl-transferase was used as marker (described in e.g. Diderichsen, B.; Poulsen, G. B.; Joergensen, S. T.; A useful cloning vector for *Bacillus subtilis*. Plasmid 30:312 (1993)). The final gene constructs were integrated on the *Bacillus* chromosome by homologous recombination into the pectate lyase locus. The gene fragments were amplified from chromosomal DNA of the corresponding strains with gene specific primers containing overhang to the two flanking vector fragments (primer sequences are listed in Table 2). All genes were expressed with a *Bacillus clausii* secretion signal (with the following amino acid sequence: MKKPLGKIV-ASTALLISVAFSSSIASA) (SEQ ID NO: 25) replacing the native secretion signal and the *Bacillus* sp-62451 genes were expressed with a poly histidine-tag (HHHHHH) SEQ ID NO: 26) linked to the C-terminal of the protein.

TABLE 2

Primers used for PCR amplification

| Template DNA | Primer forward | Primer reverse |
|---|---|---|
| *Bacillus* sp-1 SEQ ID NO 1 | GTTCATCGATCGCATCGGCTAAAGAA CCGGAGACCCAAAAT (SEQ ID NO: 11) | GCGTTTTTTTATTGATTAACGCGTTTATTT TACACGTGGGTATCCGAA (SEQ ID NO: 12) |
| *Bacillus idriensis* SEQ ID NO 3 | GTTCATCGATCGCATCGGCTCAAGAT GCGGCAAAAACAGATG (SEQ ID NO: 13) | GCGTTTTTTTATTGATTAACGCGTTTATTG TACTCTGGCAAACCCAA (SEQ ID NO: 14) |

TABLE 2-continued

Primers used for PCR amplification

| Template DNA | Primer forward | Primer reverse |
|---|---|---|
| Bacillus sp-2 SEQ ID NO 5 | TTTTAGTTCATCGATCGCATCGGCTT CAGATGAAGCAAAGGGG (SEQ ID NO: 15) | GCGTTTAGTGGTGATGGTGATGATGTTTT ACTCTAGGGTAACCAAATC (SEQ ID NO: 16) |

The two vector fragments and the gene fragment were subjected to a Splicing by Overlap Extension (SOE) PCR reaction to assemble the 3 fragments into one linear vector construct. This was done independently for each of the three genes. An aliquot of each of the three PCR products was transformed into *Bacillus subtilis*. Transformants were selected on LB agar plates supplemented with 6 μg of chloramphenicol per ml. For each construct a recombinant *Bacillus subtilis* clone containing the integrated expression construct was grown in liquid culture. The enzyme containing supernatants were harvested and the enzymes purified as described below.

Purification of Three Proteases from *Bacillus* sp.-1, *Bacillus idriensis* and *Bacillus* sp.-2

The culture broth was centrifuged (26000×g, 20 min) and the supernatant was carefully decanted from the precipitate. The supernatant was filtered through a Nalgene 0.2 μm filtration unit in order to remove the rest of the *Bacillus* host cells. The 0.2 μm filtrate was mixed 1:1 with 3.0M $(NH_4)_2SO_4$ and the mixture was applied to a Phenyl-sepharose FF (high sub) column (from GE Healthcare) equilibrated in 100 mM $H_3BO_3$, 10 mM MES/NaOH, 2 mM $CaCl_2$, 1.5M $(NH_4)_2SO_4$, pH 6.0. After washing the column with the equilibration buffer, the protease was step-eluted with 100 mM $H_3BO_3$, 10 mM MES, 2 mM $CaCl_2$, pH 6.0. The eluted peak (containing the protease activity) was collected and applied to a Bacitracin agarose column (from Upfront chromatography) equilibrated in 100 mM $H_3BO_3$, 10 mM MES, 2 mM $CaCl_2$, pH 6.0. After washing the column extensively with the equilibration buffer, the protease was eluted with 100 mM $H_3BO_3$, 10 mM MES, 2 mM $CaCl_2$, 1M NaCl, pH 6.0 with 25% (v/v) 2-propanol. The elution peak (containing the protease activity) was transferred to 20 mM MES, 2 mM $CaCl_2$, pH 6.0 on a G25 sephadex column (from GE Healthcare). The G25 transferred peak was the purified preparation and was used for further experiments.

When the purified protease preparations were analyzed by SDS-PAGE and the gel was stained with coomassie a major band was seen at approx. 36-37 kDa and two minor bands were seen at approx. 29 Da and 7-8 kDa respectively. EDMAN degradation showed that the minor bands represent nicked protease molecules. This is supported by the fact that only one band was seen on a coomasie stained SDS-PAGE gel if this gel was run without reducing agent suggesting an intramolecular sulphur bridge connecting the two parts of the nicked protease molecules.

The purified proteases were tested for activity by a protease activity assay using Suc-AAPF-pNA as substrate. The assay was performed as follows:
pNA substrate: Suc-AAPF-pNA (Bachem L-1400).
Temperature: Room temperature (25° C.)
Assay buffer: 100 mM succinic acid, 100 mM HEPES, 100 mM CHES, 100 mM CABS, 1 mM $CaCl_2$, 150 mM KCl, 0.01% Triton X-100, pH 9.0.

20 μl protease (diluted in 0.01% Triton X-100) was mixed with 100 μl assay buffer. The assay was started by adding 100 μl pNA substrate (50 mg dissolved in 1.0 ml DMSO and further diluted 45× with 0.01% Triton X-100). The initial increase in $OD_{405}$ was monitored as a measure of the protease activity.

The skilled person knows of alternative assays that may be used in order to determine the activity of a polypeptide having protease activity, or a protease as such.

Example 2: TOM Wash Using the Proteases from *Bacillus* sp.-1

The wash performance of the protease from *Bacillus* sp-1 was tested using laundry liquid model detergent on 6 different stains using the Tergo-O-Meter (TOM) wash system.

The Tergo-O-Meter (TOM) is a medium scale model wash system that can be applied to test 16 different wash conditions simultaneously. A TOM is basically a large temperature controlled water bath with up to 16 open metal beakers submerged into it. Each beaker constitutes one small top loader style washing machine, each of them containing a solution of a specific detergent/enzyme system and the soiled and unsoiled fabrics. Using the soiled and unsoiled fabrics the performance of the specific detergent/enzyme system can be determined. Mechanical stress can be achieved by a rotating stirring arm stirring the liquid within each beaker. Because the TOM beakers have no lid, withdrawal of samples during a TOM experiment is possible, and thereby facilitating the option of gathering information on-line during washing.

In a TOM experiment, factors such as 'the ballast to soil' ratio and 'the fabric to wash liquid' ratio can be varied. Therefore, the TOM provides the link between small scale experiments, such as AMSA and mini-wash, and the more time consuming full scale experiments in top loader washing machines.

The TOM experiment was performed by using a water bath comprising up to 16 steel beakers and 1 rotating arm per beaker with the capacity of 500 or 1200 mL of detergent solution. The experiment was performed in the temperature range from 5 to 80° C. The water bath was filled with deionized water, and the rotational speed was set to 70 to 120 rpm/min.

All beakers were clean and without traces of prior test material.

The wash solution was then prepared with the desired amount of detergent, temperature and water hardness in a bucket. Detergent was dissolved during magnet stirring for 10 min. The wash solution was used within 30 to 60 min after preparation. 1000 ml wash solution was added to each TOM beaker, and agitation at 120 rpm was started. To those beakers used for testing the enzymes of the present invention, the enzymes were added to the beaker. The swatches (also termed "fabrics") and the ballast (i.e. additional clean pre-washed cotton and/or polyester textile to get 'the desired liquid to textile' ratio were sprinkled and loaded to the beaker. Time measurement started when the swatches and the ballast were added to the beaker. The washing ran for 30 min and was stopped by stopping the agitation of the beakers. The wash load was transferred from the TOM beakers to a sieve in order to rinse with cold tap water. The swatches and the ballast were transferred to a European washing machine for a 14 min rinse cycle. The swatches were separated from the ballast and placed on a tray covered with a paper. Another paper was added on top of the swatches. The swatches were left to dry overnight and the Color Eye was measured as described below.

The experimental conditions are summarized in Table 3.

TABLE 3

Experimental conditions for laundry experiments

| | |
|---|---|
| Detergent dosage | Laundry liquid model detergent B 3.33 g/L |
| Test solution volume | 1 L |
| pH | As is |
| Wash time | 30 minutes |
| Temperature | 20° C. |
| Water hardness | 15° dH |
| Protease concentration | 30 nM |
| Swatch | CS-37, C-05, PC-03, CS-01, C-H010, 062KC |

Water hardness was adjusted to 15° dH by addition of CaCl$_2$, MgCl$_2$, and NaHCO$_3$ (Ca$^{2+}$:Mg$^{2+}$:CO$_3^-$ = 4:1:7.5) to the test system.

TABLE 4

Delta remission value of detergent containing proteases from *Bacillus* sp.-1 compared to detergent without protease at 20° C.

| | Swatch | | | | | |
|---|---|---|---|---|---|---|
| | CS-37 | C-05 | PC-03 | CS-01 | C-H010 | 062KC |
| *Bacillus* sp.-1 | 3.4 | 3.7 | 3.8 | 1.4 | 5.2 | 7.3 |

The results of Table 4 show that detergent containing *Bacillus* sp.-1 is effective at removing grass (062KC), egg (CS-37) chocolate/milk (C-H010, PC-03), blood/milk/ink (C-05), and blood (CS-01) stains at 20° C.

TABLE 5

Relative wash performance of detergent containing proteases from *Bacillus* sp.-1 compared to detergent TY-145 protease (SEQ ID NO 10) at 20° C.

| | Swatch<br>C-H010 |
|---|---|
| *Bacillus* sp.-1 | 1.5 |

The results of Table 5 show that detergent containing *Bacillus* sp.-1 is more effective at removing chocolate/milk (C-H010) than TY145 at 20° C.

Example 3: AMSA Wash Using the Proteases from *Bacillus* sp.-1 and *Bacillus* sp.-2

The wash performance of the proteases from *Bacillus* sp.-1 and *Bacillus* sp.-2 was tested using laundry liquid model detergent on five different technical stains using the Automatic Mechanical Stress Assay (AMSA).

By AMSA, the wash performance of many small volume enzyme-detergent solutions can be examined. The AMSA plate has a number of slots for test solutions and a lid that firmly squeezes the textile to be washed against the slot openings. During the wash, the plate, test solutions, textile and lid are vigorously shaken to bring the test solution in contact with the textile and apply mechanical stress in a regular, periodic, oscillating manner. For further description see WO02/42740 especially the paragraph "Special method embodiments" at page 23-24.

TABLE 6

Model detergents and test materials were as follows:

| | |
|---|---|
| Laundry liquid model detergent | Sodium hydroxide 99%: 2.95%<br>Sulfonic acid: 11.52%<br>Soy soap: 5.5%<br>Propylene glycole: 5.05%<br>C13-alkoholethoxylate, 8 EO: 9.45%<br>Phosphonate, Dequest 2066 type: 1.00%<br>Triethanolamine: 2.0%<br>Coco soap: 4.5%<br>Sodium citrate, dihydrate: 1.0%<br>IPA-denaturered ethanol: 4.63%<br>Opacifier: 0.12% Blue dye.<br>Ion exchanged water up to 100% |
| Laundry liquid model detergent B | LAS 7.2%<br>AEOS 4.2%<br>Soy soap 2.75%<br>Coco soap 2.75%<br>AEO 6.6%<br>NaOH 1.2%<br>Ethanol 3%<br>MPG 6%<br>Glycerol 2%<br>TEA 3%<br>Sodium formiate 1%<br>Sodium citrate 2%<br>DTMPA 0.2%<br>PCA 0.2%<br>Ion exchanged water 55.1% |
| Laundry liquid model detergent K | LAS 3%<br>AS 3%<br>AEOS 6%<br>coco fatty acid 1%<br>AEO 3%<br>MEA 0.3%<br>MPG 3%<br>Ethanol 1.5%<br>DTPA (as Na5 salt) 0.1%<br>Sodium citrate 4%<br>Sodium formate 1%<br>KOH 0.6%<br>NaOH 0.4%<br>Ion exchanged water up to 100% |
| Persil Small&Mighty | Commercially available |
| Great value Mandarin Essence | Commercially available |
| Test material | CS-37 Full egg pigment<br>C-05 Blood/milk/ink on cotton<br>PC-03 Chocolate milk/soot<br>CS-01 Aged blood<br>C-H010 Cocoa cooked up milk<br>CS-38 Egg Yolk on cotton<br>C-03 Chocolate milk/soot on cotton<br>EMPA117 Blood/milk/ink on cotton/polyester<br>062KC Scrubbed Grass on knitted cotton |

Test materials were obtained from EMPA Testmaterials AG, Mövenstrasse 12, CH-9015 St. Gallen, Switzerland, from Center For Testmaterials BV, P.O. Box 120, 3133 KT Vlaardingen, the Netherlands, and WFK Testgewebe GmbH, Christenfeld 10, D-41379 Brüggen, Germany.

Water hardness was adjusted to 15° dH by addition of CaCl$_2$, MgCl$_2$, and NaHCO$_3$ (Ca$^{2+}$:Mg$^{2+}$=4:1:7.5) to the test system. After washing the textiles were rinsed in tap water and dried.

The wash performance was measured as the brightness of the color of the textile washed. Brightness may also be expressed as the intensity of the light reflected from the sample when illuminated with white light. When the sample is stained the intensity of the reflected light is lower, than that of a clean sample. Therefore the intensity of the reflected light can be used to measure wash performance.

Color measurements were made with a professional flat-bed scanner (Kodak iQsmart, Kodak, Midtager 29, DK-2605 Brøndby, Denmark), which was used to capture an image of the washed textile.

To extract a value for the light intensity from the scanned images, 24-bit pixel values from the image were converted into values for red, green and blue (RGB). The intensity value (Int) was calculated by adding the RGB values together as vectors and then taking the length of the resulting vector:

$$Int = \sqrt{r^2 + g^2 + b^2}.$$

The experiments were conducted using a single cycle wash procedure, with the detergent composition and swatches described in Table 6 and the experimental conditions as specified in Table 7 below.

TABLE 7

Experimental conditions for laundry experiments

| | |
|---|---|
| Detergent dosage | Laundry liquid model detergent B 3.33 g/L |
| Test solution volume | 160 micro L |
| pH | As is |
| Wash time | 20 minutes |
| Temperature | 20° C. |
| Water hardness | 15° dH |
| Protease concentration | 0-10-30-60-100 nM |
| Swatch | PC-03, CS-38, CS-01, C-03 |

Water hardness was adjusted to 15° dH by addition of $CaCl_2$, $MgCl_2$, and $NaHCO_3$ ($Ca^{2+}:Mg^{2+}:CO_3^- = 4:1:7.5$) to the test system. After washing the textiles were rinsed in tap water and dried.

TABLE 8

Delta intensity value of detergent comprising proteases from *Bacillus* sp.-1 and *Bacillus* sp.-2 compared to detergent without protease at 20° C.

| | Enzyme concentration | Swatch | | | |
|---|---|---|---|---|---|
| | nM | PC-03 | CS-38 | CS-01 | C-03 |
| *Bacillus* sp.-1 | 10 | 6.0 | 4.4 | 1.4 | 0.4 |
| | 30 | 10.4 | 4.0 | 1.2 | 3.2 |
| | 60 | 12.3 | 7.6 | 2.9 | 6.7 |
| | 100 | 14.6 | 8.0 | 5.1 | 5.8 |
| *Bacillus* sp.-2 | 10 | 8.2 | 1.5 | 2.7 | 4.3 |
| | 30 | 14.6 | 5.4 | 5.2 | 4.7 |
| | 60 | 17.9 | 11.4 | 3.9 | 6.3 |
| | 100 | 18.9 | 10.3 | 6.7 | 8.4 |

The results of Table 8 show that detergent comprising *Bacillus* sp.-1 and *Bacillus* sp.-2 is effective at removing chocolate/milk (PC-03, C-03), blood (CS-01) and egg (CS-38) stains at 20° C.

Example 4: AMSA Dose-Response Wash Using the Proteases from *Bacillus* sp.-1 and *Bacillus idriensis*

The dose-response wash performance of the proteases from *Bacillus* sp.-1 and *Bacillus idriensis* was tested using four different detergents on three different stains.

The experiments were conducted as described in the AMSA for laundry method (as described in Example 3) using a single cycle wash procedure, with the detergent composition and swatches described in Table 6 and the experimental conditions as specified in Table 9 below.

TABLE 9

Experimental conditions for laundry experiments

| | |
|---|---|
| Detergent dosage | Laundry liquid model detergent B 3.33 g/L (EU detergent) |
| | Persil Small & Mighty 2.5 g/L (EU detergent) |
| | Great value Mandarin Essence 1.19 g/L (US detergent) |
| | Laundry liquid model detergent K 0.8 g/L (US detergent) |
| Test solution volume | 160 μL |
| pH | As is |
| Wash time | 20 minutes |
| Temperature | 20° C. |
| Water hardness | 15° dH (EU detergents) or 9°dH (US detergents) |
| Protease concentration | 0-2.5 nM-5 nM-10 nM-30 nM |
| Swatch | PC-03, C-05, CS-37 |

Water hardness was adjusted to 15° dH by addition of $CaCl_2$, $MgCl_2$, and $NaHCO_3$ ($Ca^{2+}:Mg^{2+}:CO_3^- = 4:1:7.5$) to the test system. After washing the textiles were flushed in tap water and dried.

TABLE 10

Performance of proteases from *Bacillus* sp.-1 and *Bacillus idriensis* on C-05 Blood/Milk/Ink stain compared to detergent without protease at 20° C.

| | Detergent | | | | | | | |
|---|---|---|---|---|---|---|---|---|
| | Laundry liquid model detergent B | | Persil Small & Mighty | | Great value Mandarin Essence | | Laundry liquid model detergent K | |
| | 10 nM | 30 nM | 10 nM | 30 nM | 10 nM | 30 nM | 10 nM | 30 nM |
| *Bacillus* sp.-1 | 13.0 | 20.1 | 16.9 | 24.8 | 4.3 | 10.6 | 6.8 | 14.1 |
| *Bacillus idriensis* | 1.33 | 3.77 | 1.4 | 0.8 | 6.2 | 3.4 | 0.4 | 3.9 |

TABLE 11

Performance of proteases from Bacillus sp.-1 and Bacillus idriensis on PC-03 Cocoa stain compared to detergent without protease at 20° C.

| | Detergent | | | | | | | |
|---|---|---|---|---|---|---|---|---|
| | Laundry liquid model detergent B | | Persil Small & Mighty | | Great value Mandarin Essence | | Laundry liquid model detergent K | |
| | 10 nM | 30 nM | 10 nM | 30 nM | 10 nM | 30 nM | 10 nM | 30 nM |
| Bacillus sp.-13380 | 7.5 | 12.7 | 8.4 | 15.0 | 2.1 | 4.3 | 2.4 | 7.4 |
| Bacillus idriensis | 0.6 | 0.7 | 2.2 | 2.1 | 0 | 0 | 0 | 1.0 |

TABLE 12

Performance of proteases from Bacillus sp.-1 and Bacillus idriensis on CS-37 Full Egg w/Pigment stain compared to detergent without protease at 20° C.

| | Detergent | | | | | | | |
|---|---|---|---|---|---|---|---|---|
| | Laundry liquid model detergent B | | Persil Small & Mighty | | Great value Mandarin Essence | | Laundry liquid model detergent K | |
| | 10 nM | 30 nM | 10 nM | 30 nM | 10 nM | 30 nM | 10 nM | 30 nM |
| Bacillus sp.-1 | 1.8 | 3.3 | 4.1 | 4.8 | 0 | 0.8 | 3.4 | 8.3 |
| Bacillus idriensis | 1.6 | 1.4 | 0.8 | 2.0 | 0.5 | 0 | 0 | 1.8 |

The results of Tables 10, 11, and 12 show that detergents comprising Bacillus sp.-1 is particular effective at removing chocolate/milk, blood/milk and egg stains at 20° C.

Example 5: Mini Wash Using the Proteases from Bacillus sp.-1

The wash performance of the proteases from Bacillus sp.-1 was tested using laundry liquid model detergent on one technical stain using the mini wash system, which is a test method where soiled textile is continuously lifted up and down into the test solution and subsequently rinsed.

TABLE 13

| The experimental conditions | |
|---|---|
| Detergent | Laundry liquid model detergent Laundry liquid model detergent B |
| Detergent dose | 8 g/l 3.33 g/L |
| pH | As is (i.e. not adjusted) |
| Water hardness | 15°dH, adjusted by adding $CaCl_2 * 2H_2O$, $MgCl_2 * 6H_2O$ and $NaHCO_3$ (4:1:7.5) to milli-Q water. |
| Enzyme conc. | 2.5 nM, 5 nM, 10 nM, 30 nM, 60 nM |
| Test solution volume | 50 mL |
| Test material | PC-03 Chocolate milk/soot |
| Temperature | 30° C. |
| Wash time | 20 min |
| Rinse time | 10 min |
| Test system | Soiled textile continuously lifted up and down into the test solutions, 50 times per minute (up-time 0.29 sec, down-time 0.29 sec, lift time 0.17 sec). The test solutions are kept in 125 ml glass beakers. After wash of the textiles are continuously lifted up and down into tap water, 50 times per minute (up-time 0.5 sec, down-time 5 sec, lift time 0.5 sec). |

Test materials were obtained from EMPA Testmaterials AG Mövenstrasse 12, CH-9015 St. Gallen, Switzerland, from Center for Testmaterials By, P.O. Box 120, 3133 KT Vlaardingen, the Netherlands, and WFK Testgewebe GmbH, Christenfeld 10, D-41379 Brüggen, Germany.

The textiles were subsequently air-dried and the wash performance was measured as the brightness of the color of these textiles. Brightness may also be expressed as the Remission (R), which is a measure for the light reflected or emitted from the test material when illuminated with white light. The Remission (R) of the textiles was measured at 460 nm using a Zeiss MCS 521 VIS spectrophotometer. The measurements were done according to the manufacturer's protocol.

The performance of the proteases of the invention was compared to the performance of proteases at 30 nM protease concentration by calculating the relative performance:

$$RP=(R_{protease}-R_{BLANK})/(R_{REFERENCE}-R_{BLANK})$$

An enzyme was considered to exhibit improved wash performance, if it performed better than the reference (RP>1) in at least one detergent composition.
The experimental conditions are specified in Table 14 below.

TABLE 14

Delta remission value of detergent containing proteases from *Bacillus* sp.-1 compared to detergent without protease at 30° C. on chocolate (PC-03).

| Detergent | Enzyme dosage nM | Laundry liquid model detergent | Laundry liquid model detergent B |
|---|---|---|---|
| *Bacillus* sp.-1 | 0 | 0 | 0 |
| | 0.5 | 0.3 | 0 |
| | 1.1 | 0.6 | 0.3 |
| | 2.1 | 1.4 | 1.3 |

TABLE 14-continued

Delta remission value of detergent containing proteases from *Bacillus* sp.-1 compared to detergent without protease at 30° C. on chocolate (PC-03).

| Detergent | Enzyme dosage nM | Laundry liquid model detergent | Laundry liquid model detergent B |
|---|---|---|---|
| | 4.3 | 2.3 | 1.6 |
| | 12.8 | 4.3 | 2.6 |

The results of Table 14 show that an enzyme dosage of 2.1 nM has an improved wash performance even at such low dosages (i.e. commercial available detergent compositions may comprise up to 30-90 nM enzymes depending on the region).

The invention claimed is:

1. An isolated recombinant host cell comprising a nucleic acid construct or expression vector comprising a polynucleotide encoding a polypeptide having protease activity and one or more heterologous control sequences that direct the production of the polypeptide in the recombinant host cell, wherein the amino acid sequence of the polypeptide has at least 85% sequence identity to the amino acid sequence of amino acids 1 to 314 of SEQ ID NO: 4; and the polynucleotide is operably linked to the one or more heterologous control sequences that direct the production of the polypeptide in the recombinant host cell.

2. The recombinant host cell of claim 1, wherein the amino acid sequence of the polypeptide has at least 90% sequence identity to the amino acid sequence of amino acids 1 to 314 of SEQ ID NO: 4.

3. The recombinant host cell of claim 1, wherein the amino acid sequence of the polypeptide has at least 95% sequence identity to the amino acid sequence of amino acids 1 to 314 of SEQ ID NO: 4.

4. The recombinant host cell of claim 1, wherein the polypeptide is encoded by a polynucleotide comprising a nucleotide sequence having at least 85% sequence identity to nucleotide sequence of nucleotides 810 to 1751 of SEQ ID NO: 3.

5. The recombinant host cell of claim 1, wherein the polypeptide is a fragment of the amino acid sequence of amino acids 1 to 314 of SEQ ID NO: 4, wherein the fragment has protease activity.

6. The recombinant host cell of claim 1, wherein the polypeptide comprises or consists of the amino acid sequence of amino acids 1 to 314 of SEQ ID NO: 4.

7. A method of producing a polypeptide having protease activity comprising:
   (a) cultivating the recombinant host cell of claim 1 under conditions conducive for production of the polypeptide; and
   (b) recovering the polypeptide.

8. A method of producing a polypeptide having protease activity comprising:
   (a) cultivating the recombinant host cell of claim 2 under conditions conducive for production of the polypeptide; and
   (b) recovering the polypeptide.

9. A method of producing a polypeptide having protease activity comprising:
   (a) cultivating the recombinant host cell of claim 3 under conditions conducive for production of the polypeptide; and
   (b) recovering the polypeptide.

10. A method of producing a polypeptide having protease activity comprising:
    (a) cultivating the recombinant host cell of claim 4 under conditions conducive for production of the polypeptide; and
    (b) recovering the polypeptide.

11. A method of producing a polypeptide having protease activity comprising:
    (a) cultivating the recombinant host cell of claim 5 under conditions conducive for production of the polypeptide; and
    (b) recovering the polypeptide.

12. A method of producing a polypeptide having protease activity comprising:
    (a) cultivating the recombinant host cell of claim 6 under conditions conducive for production of the polypeptide; and
    (b) recovering the polypeptide.

13. The method of claim 7, wherein the recombinant host cell is a *Bacillus* recombinant host cell.

* * * * *

SEQUENCE LISTING

```
<160> NUMBER OF SEQ ID NOS: 27

<210> SEQ ID NO 1
<211> LENGTH: 2272
<212> TYPE: DNA
<213> ORGANISM: bacillus sp.
<220> FEATURE:
<221> NAME/KEY: CDS
<222> LOCATION: (501)..(1769)
<220> FEATURE:
<221> NAME/KEY: sig_peptide
<222> LOCATION: (501)..(581)
<220> FEATURE:
<221> NAME/KEY: mat_peptide
<222> LOCATION: (831)..(1769)

<400> SEQUENCE: 1
tgtaagaacc tataatcccg cattcgatgt aacagatagt gaactgatca caggcattat      60
cacggaaaat ggcatcgcgt atgcaccttta cacagaaagc cttcctaaga tgttcaaata    120
agaagaaata gcctcctgac caagcggtta ggaggatttt tattcttcat atctttaaag    180
cgtttaacta ggaaaatatc cctgacatca ataaaaacga agtgtaattt cactctttgt    240
atctatcaaa ggaactaatt tttttggggt aatttattta tttctggaaa tattatgaat    300 ttaacacat atgtatagtg gaaaaaattt gtaaatcagt caaaatgcct gttacttttt     360
gagaagctat gtttctatgc ctgattctaa agtctgagaa ttaaacattt tagcatattg    420
ttagagtctg aatattttaa atatacttga aatacaacag gaatcgacag aaaaaatata    480
gacttgagag gagaaaaagg atg aag aaa aaa agg gca tta gga gca gca        530
                       Met Lys Lys Lys Arg Ala Leu Gly Ala Ala
                              -110                  -105 ctt cta agt atg acc atg ggt tta tca gtt ttc aca gcg ggg gca ttc      578
Leu Leu Ser Met Thr Met Gly Leu Ser Val Phe Thr Ala Gly Ala Phe
-100                  -95                  -90                  -85 gct aaa gaa ccg gag acc caa aat gaa acc tac cgg gta tta atc cag      626
Ala Lys Glu Pro Glu Thr Gln Asn Glu Thr Tyr Arg Val Leu Ile Gln
                -80                  -75                  -70 ggt ccg gca aat gct aaa gcc agt gtg aat tca cag gtg gac aag cgt      674
Gly Pro Ala Asn Ala Lys Ala Ser Val Asn Ser Gln Val Asp Lys Arg
            -65                  -60                  -55 tgg gat ttt ggc agc gat ggc atg act gca gag gtt aat gct aag caa      722
Trp Asp Phe Gly Ser Asp Gly Met Thr Ala Glu Val Asn Ala Lys Gln
        -50                  -45                  -40
```

-continued

| | | |
|---|---|---|
| tac cag gca ctc ctg aaa aat aag aac tta aag att gaa aaa gta agc<br>Tyr Gln Ala Leu Leu Lys Asn Lys Asn Leu Lys Ile Glu Lys Val Ser<br>             -35                      -30                     -25 | 770 | |
| gaa gtt act ctt gat act gcc aga aca gag gcg tcc aag aaa gat tca<br>Glu Val Thr Leu Asp Thr Ala Arg Thr Glu Ala Ser Lys Lys Asp Ser<br>-20                   -15                      -10                      -5 | 818 | |
| gtt tct att cag gca gca ggg tat cct agt gat caa aca cca tgg gga<br>Val Ser Ile Gln Ala Ala Gly Tyr Pro Ser Asp Gln Thr Pro Trp Gly<br>             -1   1                 5                       10 | 866 | |
| att gct tca atc tat aat aac agc agc att acg agt acg tca ggc gga<br>Ile Ala Ser Ile Tyr Asn Asn Ser Ser Ile Thr Ser Thr Ser Gly Gly<br>          15                     20                     25 | 914 | |
| agc ggc att aag gtt gca gtt ctt gat acg ggc gtt tat acc ggt cat<br>Ser Gly Ile Lys Val Ala Val Leu Asp Thr Gly Val Tyr Thr Gly His<br>     30                     35                     40 | 962 | |
| att gac ctg gaa ggc tct gcg gag caa tgt aaa gac ttc act caa tcc<br>Ile Asp Leu Glu Gly Ser Ala Glu Gln Cys Lys Asp Phe Thr Gln Ser<br>45                  50                     55                    60 | 1010 | |
| act ccg ctt gta aat ggt tct tgt acg gat cgc cag ggc cat gga aca<br>Thr Pro Leu Val Asn Gly Ser Cys Thr Asp Arg Gln Gly His Gly Thr<br>                       65                     70                     75 | 1058 | |
| cat gta gcc ggg acg gtt ttg gca cat gga gga tat gat ggc cag ggg<br>His Val Ala Gly Thr Val Leu Ala His Gly Gly Tyr Asp Gly Gln Gly<br>          80                     85                     90 | 1106 | |
| att tat gga gtt gct cca cag gcg aag tta tgg gca tat aaa gtc ctt<br>Ile Tyr Gly Val Ala Pro Gln Ala Lys Leu Trp Ala Tyr Lys Val Leu<br>             95                   100                  105 | 1154 | |
| gga gat aat ggt tcg gga tat tca gat gat att gca gga gca atc cgc<br>Gly Asp Asn Gly Ser Gly Tyr Ser Asp Asp Ile Ala Gly Ala Ile Arg<br>110                  115                    120 | 1202 | |
| cac gta gcg gac gaa gca tcc cgt act ggt tct aaa gtg gtc atc aac<br>His Val Ala Asp Glu Ala Ser Arg Thr Gly Ser Lys Val Val Ile Asn<br>125                  130                    135                140 | 1250 | |
| atg tcc ctt ggt tca agc ggc aag gac tcc ctc atc agc agt gcg gtt<br>Met Ser Leu Gly Ser Ser Gly Lys Asp Ser Leu Ile Ser Ser Ala Val<br>                    145                    150                155 | 1298 | |
| gat tac gca tac agc aaa ggt gtc ctt gtt gtt gct gca gca gga aac<br>Asp Tyr Ala Tyr Ser Lys Gly Val Leu Val Val Ala Ala Ala Gly Asn<br>160                  165                    170 | 1346 | |
| tca ggc tac agc gct aat aca atc ggc tat cct gga gct tta aag aat<br>Ser Gly Tyr Ser Ala Asn Thr Ile Gly Tyr Pro Gly Ala Leu Lys Asn<br>          175                    180                  185 | 1394 | |
| gcg atc gcg gtt gca gct ctt gaa aac gtt cag caa aac ggt aca tac<br>Ala Ile Ala Val Ala Ala Leu Glu Asn Val Gln Gln Asn Gly Thr Tyr<br>190                  195                    200 | 1442 | |
| cgt gta gcc aac ttc tca tcc cgc gga aat cct aac acg gac ggt gac<br>Arg Val Ala Asn Phe Ser Ser Arg Gly Asn Pro Asn Thr Asp Gly Asp<br>205                  210                    215                220 | 1490 | |
| tat atc att cag gaa aaa gac gtg gaa gtg tct gca cct ggt gca agc<br>Tyr Ile Ile Gln Glu Lys Asp Val Glu Val Ser Ala Pro Gly Ala Ser<br>                    225                    230                235 | 1538 | |
| atc gag tct acg tgg tat aac gga ggc tat aac acg atc agc gga aca<br>Ile Glu Ser Thr Trp Tyr Asn Gly Gly Tyr Asn Thr Ile Ser Gly Thr<br>240                  245                    250 | 1586 | |
| tcc atg gca aca cct cac gta gca ggc ctt gca gca aag att tgg tct<br>Ser Met Ala Thr Pro His Val Ala Gly Leu Ala Ala Lys Ile Trp Ser<br>          255                    260                  265 | 1634 | |
| tcc agc cca tcc atg agc cac act cag ctt cgc aca gag ctt caa aat<br>Ser Ser Pro Ser Met Ser His Thr Gln Leu Arg Thr Glu Leu Gln Asn<br>                    270                    275                280 | 1682 | |

```
cgt gcc aag caa tat gac ata aaa ggc gga tac gga gca gca act ggt      1730
Arg Ala Lys Gln Tyr Asp Ile Lys Gly Gly Tyr Gly Ala Ala Thr Gly
285                 290                 295                 300 gat gac tat gcg tcg ggc ttc gga tac cca cgt gta aaa taaacgaaca        1779
Asp Asp Tyr Ala Ser Gly Phe Gly Tyr Pro Arg Val Lys
                305                 310 gaagcatacc ccgataaacc gtctgatctc tcatcaggcg ttttttttaa tatttccgcg    1839
gaaatgatca aattttggcg aaacaagaaa actaatagaa aatgctgaaa caattttatt    1899
ttgaatatac aatagggagt ggatgtgaat aggaagggag ctggcagcca tggctgttca    1959
taatacatat cttaatgacc aggaagcaaa ggaattcatc tgcgaaatcg cagaagaat     2019 atacaataaa aacttcgttg ctgcaaacga cggaaacatt tccattaaag tgaatgaccg    2079
tgaactttgg acatcaccaa ccggagtgag caaagggttt atgacaccgg atatgatggt    2139
taagatggac ctttcaggta atgtcctgga aggagagctg aagccttctt cagaagtaaa    2199
gatgcacctt agagtgtatc aggaaaatac tgaagcaaaa gctgttgtcc atgcccatcc    2259
gcctgttgca act                                                       2272

<210> SEQ ID NO 2
<211> LENGTH: 423
<212> TYPE: PRT
<213> ORGANISM: bacillus sp.

<400> SEQUENCE: 2

Met Lys Lys Lys Arg Ala Leu Gly Ala Ala Leu Leu Ser Met Thr
-110                -105                -100

Met Gly Leu Ser Val Phe Thr Ala Gly Ala Phe Ala Lys Glu Pro Glu
-95                 -90                 -85                 -80

Thr Gln Asn Glu Thr Tyr Arg Val Leu Ile Gln Gly Pro Ala Asn Ala
                -75                 -70                 -65

Lys Ala Ser Val Asn Ser Gln Val Asp Lys Arg Trp Asp Phe Gly Ser
                -60                 -55                 -50

Asp Gly Met Thr Ala Glu Val Asn Ala Lys Gln Tyr Gln Ala Leu Leu
            -45                 -40                 -35

Lys Asn Lys Asn Leu Lys Ile Glu Lys Val Ser Glu Val Thr Leu Asp
        -30                 -25                 -20

Thr Ala Arg Thr Glu Ala Ser Lys Lys Asp Ser Val Ser Ile Gln Ala
-15                 -10                 -5                  -1  1

Ala Gly Tyr Pro Ser Asp Gln Thr Pro Trp Gly Ile Ala Ser Ile Tyr
                5                   10                  15

Asn Asn Ser Ser Ile Thr Ser Thr Ser Gly Gly Ser Gly Ile Lys Val
                20                  25                  30

Ala Val Leu Asp Thr Gly Val Tyr Thr Gly His Ile Asp Leu Glu Gly
                35                  40                  45

Ser Ala Glu Gln Cys Lys Asp Phe Thr Gln Ser Thr Pro Leu Val Asn
50                  55                  60                  65

Gly Ser Cys Thr Asp Arg Gln Gly His Gly Thr His Val Ala Gly Thr
                70                  75                  80

Val Leu Ala His Gly Gly Tyr Asp Gly Gln Gly Ile Tyr Gly Val Ala
                85                  90                  95

Pro Gln Ala Lys Leu Trp Ala Tyr Lys Val Leu Gly Asp Asn Gly Ser
                100                 105                 110

Gly Tyr Ser Asp Asp Ile Ala Gly Ala Ile Arg His Val Ala Asp Glu
                115                 120                 125
```

Ala Ser Arg Thr Gly Ser Lys Val Val Ile Asn Met Ser Leu Gly Ser
130             135                 140                 145

Ser Gly Lys Asp Ser Leu Ile Ser Ala Val Asp Tyr Ala Tyr Ser
        150                 155                 160

Lys Gly Val Leu Val Val Ala Ala Gly Asn Ser Gly Tyr Ser Ala
            165                 170                 175

Asn Thr Ile Gly Tyr Pro Gly Ala Leu Lys Asn Ala Ile Ala Val Ala
        180                 185                 190

Ala Leu Glu Asn Val Gln Gln Asn Gly Thr Tyr Arg Val Ala Asn Phe
    195                 200                 205

Ser Ser Arg Gly Asn Pro Asn Thr Asp Gly Asp Tyr Ile Ile Gln Glu
210             215                 220                 225

Lys Asp Val Glu Val Ser Ala Pro Gly Ala Ser Ile Glu Ser Thr Trp
            230                 235                 240

Tyr Asn Gly Gly Tyr Asn Thr Ile Ser Gly Thr Ser Met Ala Thr Pro
            245                 250                 255

His Val Ala Gly Leu Ala Ala Lys Ile Trp Ser Ser Pro Ser Met
        260                 265                 270

Ser His Thr Gln Leu Arg Thr Glu Leu Gln Asn Arg Ala Lys Gln Tyr
275             280                 285

Asp Ile Lys Gly Gly Tyr Gly Ala Ala Thr Gly Asp Asp Tyr Ala Ser
290             295                 300                 305

Gly Phe Gly Tyr Pro Arg Val Lys
            310

<210> SEQ ID NO 3
<211> LENGTH: 2254
<212> TYPE: DNA
<213> ORGANISM: Bacillus idriensis
<220> FEATURE:
<221> NAME/KEY: CDS
<222> LOCATION: (501)..(1751)
<220> FEATURE:
<221> NAME/KEY: sig_peptide
<222> LOCATION: (501)..(581)
<220> FEATURE:
<221> NAME/KEY: mat_peptide
<222> LOCATION: (810)..(1751)

<400> SEQUENCE: 3

| | |
|---|---|
| ttataatcat ggcaataaaa gaataagttc gcttaaccat cctgtatgag ggatggtttt | 60 |
| tgttagtcc tgttatcgtt aagtttgtag agtaagaaat aataaagca ataaatggat | 120 |
| tgcagcggaa aggaacagac aacatttatc atgaaaaaca acaatctatg cgaaaacagc | 180 |
| ctaaaacaaa caagtagtgg agaattaaaa aaactcctaa ttaatgataa tccagtagaa | 240 |
| aactaacttt gaaagcggcc ctttcatttg tcacagaaaa taaatgatat ttcgagtttt | 300 |
| tttgcagctg ctgtacggta attaccggaa aaacaggctg tttgcgtgat agccaatgaa | 360 |
| aacccgtatc atttagcata ttaatttcta aaaatttta gttaatttag attattgtga | 420 |
| aaatagtta aaataatata tactgatttt gtttcaaagt aaaagttata tatcactaac | 480 |
| attttgaaag gggaaatgaa atg aag atc agg aag gtg ctt gga gtt gct | 530 |
|                        Met Lys Ile Arg Lys Val Leu Gly Val Ala | |
|                        -100                -95 | |
| gta tta agt tta tca atg agt ctt tca atg ttt ggc aca aac acg ttt | 578 |
| Val Leu Ser Leu Ser Met Ser Leu Ser Met Phe Gly Thr Asn Thr Phe | |
|     -90                -85                -80 | |

-continued

| | | |
|---|---|---|
| gca caa gat gcg gca aaa aca gat gta aat cag gat tcg att cgt gtc<br>Ala Gln Asp Ala Ala Lys Thr Asp Val Asn Gln Asp Ser Ile Arg Val<br>　　　-75　　　　　　　-70　　　　　　　　-65 | 626 |
| gtg atc aaa gga acg gat aca gag aaa gtc aaa atg aag aag agt cat<br>Val Ile Lys Gly Thr Asp Thr Glu Lys Val Lys Met Lys Lys Ser His<br>-60　　　　　　　-55　　　　　　　-50 | 674 |
| aaa gtt cgc agg gat ttc gga aaa gat gga ttt acg aca aca gtc aat<br>Lys Val Arg Arg Asp Phe Gly Lys Asp Gly Phe Thr Thr Thr Val Asn<br>-45　　　　　　　-40　　　　　　　-35　　　　　　　-30 | 722 |
| gcc aag gaa tac gaa gca ttg ata aaa aat gac aaa atc aag gta gaa<br>Ala Lys Glu Tyr Glu Ala Leu Ile Lys Asn Asp Lys Ile Lys Val Glu<br>　　　　-25　　　　　　　-20　　　　　　　-15 | 770 |
| aag gtt tca aca ctt caa gta gct gcc ggc aaa cca att aaa acg atg<br>Lys Val Ser Thr Leu Gln Val Ala Ala Gly Lys Pro Ile Lys Thr Met<br>　　　　　　-10　　　　　　　-5　　　　　　　　-1　1 | 818 |
| gcg ctt cca agc act aga aca cca tgg ggt att aaa gca atc tat aat<br>Ala Leu Pro Ser Thr Arg Thr Pro Trp Gly Ile Lys Ala Ile Tyr Asn<br>　　　5　　　　　　　　10　　　　　　　　15 | 866 |
| aat agc tct ctt aca tcc act tct gga gga gat ggc att aaa atc gcc<br>Asn Ser Ser Leu Thr Ser Thr Ser Gly Gly Asp Gly Ile Lys Ile Ala<br>20　　　　　　　　25　　　　　　　　30　　　　　　　　35 | 914 |
| gta ctt gat aca ggt gta caa aca agt cat att gat tta tcg caa aat<br>Val Leu Asp Thr Gly Val Gln Thr Ser His Ile Asp Leu Ser Gln Asn<br>　　　　　　　　40　　　　　　　　45　　　　　　　　50 | 962 |
| gta gag caa tgt aag gat ttc aca gtt ggc agt tct tat acg aat gga<br>Val Glu Gln Cys Lys Asp Phe Thr Val Gly Ser Ser Tyr Thr Asn Gly<br>　　　　　　55　　　　　　　　60　　　　　　　　65 | 1010 |
| tct tgt aca gac cgg aat gga cat gga act cat gta gcg gga act gct<br>Ser Cys Thr Asp Arg Asn Gly His Gly Thr His Val Ala Gly Thr Ala<br>　　　70　　　　　　　　75　　　　　　　　80 | 1058 |
| ctt gct aat ggc gga tca gat gga atg ggg att tat gga gtt gct ccg<br>Leu Ala Asn Gly Gly Ser Asp Gly Met Gly Ile Tyr Gly Val Ala Pro<br>85　　　　　　　　90　　　　　　　　95 | 1106 |
| caa tca gaa ctt tgg gct tat aaa gtg tta aca gac agc ggt tca ggc<br>Gln Ser Glu Leu Trp Ala Tyr Lys Val Leu Thr Asp Ser Gly Ser Gly<br>100　　　　　　　105　　　　　　　　110　　　　　　　115 | 1154 |
| tac tca gat gac att gca gca gca atc aga cat gca gcg gac gaa gga<br>Tyr Ser Asp Asp Ile Ala Ala Ala Ile Arg His Ala Ala Asp Glu Gly<br>　　　　　　　120　　　　　　　125　　　　　　　130 | 1202 |
| acg cgt act ggt tca aaa gtc atc att tcc atg tct ctt gga tca agc<br>Thr Arg Thr Gly Ser Lys Val Ile Ile Ser Met Ser Leu Gly Ser Ser<br>　　　　　　135　　　　　　　140　　　　　　　　145 | 1250 |
| ggt aaa gat agt tta ata gca agc gcc gtt gac tac gca tat gga aaa<br>Gly Lys Asp Ser Leu Ile Ala Ser Ala Val Asp Tyr Ala Tyr Gly Lys<br>　　　　　　150　　　　　　　155　　　　　　　　160 | 1298 |
| ggt gca tta gtc att gca gct gcg ggg aac tca ggg tct gga aat aac<br>Gly Ala Leu Val Ile Ala Ala Ala Gly Asn Ser Gly Ser Gly Asn Asn<br>　　　165　　　　　　　170　　　　　　　　175 | 1346 |
| acg att gga tat cct ggg gca ctt gtc aat gct gta gca gtt gca gca<br>Thr Ile Gly Tyr Pro Gly Ala Leu Val Asn Ala Val Ala Val Ala Ala<br>180　　　　　　　185　　　　　　　　190　　　　　　　195 | 1394 |
| ctt gaa aat gtc cag caa aac ggc acg tat cgg gtt gcg aat ttc tct<br>Leu Glu Asn Val Gln Gln Asn Gly Thr Tyr Arg Val Ala Asn Phe Ser<br>　　　　　　200　　　　　　　205　　　　　　　　210 | 1442 |
| tca cgc gga aac tct gca aca gat ggg gat ttt atc att ggt gaa cgc<br>Ser Arg Gly Asn Ser Ala Thr Asp Gly Asp Phe Ile Ile Gly Glu Arg<br>　　　　　　215　　　　　　　220　　　　　　　　225 | 1490 |
| gat gtt gaa att tca gct cca gga gca agc att gag tct aca tgg ata<br>Asp Val Glu Ile Ser Ala Pro Gly Ala Ser Ile Glu Ser Thr Trp Ile<br>　　　230　　　　　　　235　　　　　　　　240 | 1538 |

-continued

```
aat agc ggc tac aac acg atc agc ggc aca tcc atg gct act cct cat     1586
Asn Ser Gly Tyr Asn Thr Ile Ser Gly Thr Ser Met Ala Thr Pro His
    245                 250                 255 gtc tca ggg ctt gca gcg aaa att tgg tct tca aat aaa agc caa agc     1634
Val Ser Gly Leu Ala Ala Lys Ile Trp Ser Ser Asn Lys Ser Gln Ser
260                 265                 270                 275 aac gta caa gtg cgt gct gag ctt caa aac cgt gca aaa ctt tat gac     1682
Asn Val Gln Val Arg Ala Glu Leu Gln Asn Arg Ala Lys Leu Tyr Asp
                280                 285                 290 atc aaa ggc ggc ata ggc gct gca aca ggc gat gac cat gct tca ggc     1730
Ile Lys Gly Gly Ile Gly Ala Ala Thr Gly Asp Asp His Ala Ser Gly
            295                 300                 305 ttt ggg ttt gcc aga gta caa taaatagatt aatgaagatt aaaagagagc       1781
Phe Gly Phe Ala Arg Val Gln
        310 ttccttctat atttcaagga agctcttttt tgtataaata aaaatacaaa atttggttca   1841 tagctgcgaa aatatgtttt aatagagtaa atatacaagt gcagaaaaga agtgcgtaag   1901 gggcaggaaa ttaagcgtat tggacaggtt tgatgattct tggccattct tcatcagccg   1961 tttgaatatt tgcttctgtt tttgagaagc cagttaagat aatcgccgtt ccaagagcca   2021 gtaataataa gtgcatttta atcttcttca tcccattacc tcccgtattt ctgttgtaat   2081 ttaacattta aaaatcggtg atattttgtt ataattgact gacaatttaa atatatacaa   2141 ttcttttaat tattgtcaat acataattaa aaaattttca gggggcgctg tatgaatacc   2201 gttgggatga aattaagaca gctgagaaaa aaacagaaac tgactcaaaa tga          2254

<210> SEQ ID NO 4
<211> LENGTH: 417
<212> TYPE: PRT
<213> ORGANISM: Bacillus idriensis

<400> SEQUENCE: 4

Met Lys Ile Arg  Lys Val Leu Gly Val Ala Val Leu Ser Leu Ser Met
            -100                 -95                 -90

Ser Leu Ser Met Phe Gly Thr Asn Thr Phe Ala Gln Asp Ala Ala Lys
        -85                 -80                 -75

Thr Asp Val Asn Gln Asp Ser Ile Arg Val Val Ile Lys Gly Thr Asp
    -70                 -65                 -60

Thr Glu Lys Val Lys Met Lys Lys Ser His Lys Val Arg Arg Asp Phe
-55                 -50                 -45                 -40

Gly Lys Asp Gly Phe Thr Thr Thr Val Asn Ala Lys Glu Tyr Glu Ala
                -35                 -30                 -25

Leu Ile Lys Asn Asp Lys Ile Lys Val Glu Lys Val Ser Thr Leu Gln
            -20                 -15                 -10

Val Ala Ala Gly Lys Pro Ile Lys Thr Met Ala Leu Pro Ser Thr Arg
        -5              -1  1               5

Thr Pro Trp Gly Ile Lys Ala Ile Tyr Asn Asn Ser Ser Leu Thr Ser
10                  15                  20                  25

Thr Ser Gly Gly Asp Gly Ile Lys Ile Ala Val Leu Asp Thr Gly Val
                30                  35                  40

Gln Thr Ser His Ile Asp Leu Ser Gln Asn Val Glu Gln Cys Lys Asp
            45                  50                  55

Phe Thr Val Gly Ser Ser Tyr Thr Asn Gly Ser Cys Thr Asp Arg Asn
        60                  65                  70

Gly His Gly Thr His Val Ala Gly Thr Ala Leu Ala Asn Gly Gly Ser
    75                  80                  85
```

Asp Gly Met Gly Ile Tyr Gly Val Ala Pro Gln Ser Glu Leu Trp Ala
 90                  95                 100                 105

Tyr Lys Val Leu Thr Asp Ser Gly Ser Gly Tyr Ser Asp Asp Ile Ala
                110                 115                 120

Ala Ala Ile Arg His Ala Ala Asp Glu Gly Thr Arg Thr Gly Ser Lys
            125                 130                 135

Val Ile Ile Ser Met Ser Leu Gly Ser Ser Gly Lys Asp Ser Leu Ile
        140                 145                 150

Ala Ser Ala Val Asp Tyr Ala Tyr Gly Lys Gly Ala Leu Val Ile Ala
    155                 160                 165

Ala Ala Gly Asn Ser Gly Ser Gly Asn Asn Thr Ile Gly Tyr Pro Gly
170                 175                 180                 185

Ala Leu Val Asn Ala Val Ala Val Ala Ala Leu Glu Asn Val Gln Gln
                190                 195                 200

Asn Gly Thr Tyr Arg Val Ala Asn Phe Ser Ser Arg Gly Asn Ser Ala
                205                 210                 215

Thr Asp Gly Asp Phe Ile Ile Gly Glu Arg Asp Val Glu Ile Ser Ala
            220                 225                 230

Pro Gly Ala Ser Ile Glu Ser Thr Trp Ile Asn Ser Gly Tyr Asn Thr
        235                 240                 245

Ile Ser Gly Thr Ser Met Ala Thr Pro His Val Ser Gly Leu Ala Ala
250                 255                 260                 265

Lys Ile Trp Ser Ser Asn Lys Ser Gln Ser Asn Val Gln Val Arg Ala
                270                 275                 280

Glu Leu Gln Asn Arg Ala Lys Leu Tyr Asp Ile Lys Gly Gly Ile Gly
                285                 290                 295

Ala Ala Thr Gly Asp Asp His Ala Ser Gly Phe Gly Phe Ala Arg Val
            300                 305                 310

Gln

<210> SEQ ID NO 5
<211> LENGTH: 2263
<212> TYPE: DNA
<213> ORGANISM: Bacillus sp.
<220> FEATURE:
<221> NAME/KEY: sig_peptide
<222> LOCATION: (501)..(587)
<220> FEATURE:
<221> NAME/KEY: CDS
<222> LOCATION: (501)..(1760)
<220> FEATURE:
<221> NAME/KEY: mat_peptide
<222> LOCATION: (819)..(1760)

<400> SEQUENCE: 5
atttgccaga ttagaacaag cgaaacaact agggaaaatc gtgtttcaaa tagataaatg    60
actaataaga gtgaacgaaa aaattaaaaa acttcgttca ctctttttt tatccaacat   120 aaaaaatcgt cggatattgt atccgctaaa aaataagtg ctttcttaa agggaaggag   180 ctcaaaaatc actatttcct tcaaattcat gaaaataat gatgtaatat tacactttta   240
tacctttcta gagacctaaa ttcacttta attccgagta ataaaaggg taattatcat   300 gaatattgat ttatggaaa aaataactg atttaatgtt aaaaaaatg tctgatggcc   360 tgctacttgg aaaaaatat gtcaaattta ctgtttttta caaataaata aatgctgaat   420
tttacacatt gttgtagtct gaattttga aatataatta cccctaagta agacattaaa   480

```
atatgggag gaacaagtaa atg acg aaa aag aaa aca gta gca gct gca         530
                     Met Thr Lys Lys Lys Thr Val Ala Ala Ala
                        -105            -100 cta ctt agt ctt acg tta ggg atg tcc gta ttt aca tca ggt att tct     578
Leu Leu Ser Leu Thr Leu Gly Met Ser Val Phe Thr Ser Gly Ile Ser
    -95             -90             -85 gca caa gtt tca gat gaa gca aag ggg agt gaa aca tat cgc gta ttg     626
Ala Gln Val Ser Asp Glu Ala Lys Gly Ser Glu Thr Tyr Arg Val Leu
-80             -75             -70                     -65 ata caa gcc cct agc aat tct gtt aat gca tta gaa aca aag tat gaa     674
Ile Gln Ala Pro Ser Asn Ser Val Asn Ala Leu Glu Thr Lys Tyr Glu
                -60              -55            -50 aaa cga tgg gac ttt ggt aaa gaa ggt ttc act gca gat gtg aat gct     722
Lys Arg Trp Asp Phe Gly Lys Glu Gly Phe Thr Ala Asp Val Asn Ala
            -45             -40             -35 aag gag tta caa aca tta caa gcg aca aaa aat gtc gaa gta caa aag     770
Lys Glu Leu Gln Thr Leu Gln Ala Thr Lys Asn Val Glu Val Gln Lys
        -30             -25             -20 gta aat gaa atg agt ata gca acg gta aca gga gaa gtg tcg aaa gca     818
Val Asn Glu Met Ser Ile Ala Thr Val Thr Gly Glu Val Ser Lys Ala
    -15             -10             -5                      -1 gaa gta aca gct gtg cca agt tca caa aca cct tgg gga ata aaa tca     866
Glu Val Thr Ala Val Pro Ser Ser Gln Thr Pro Trp Gly Ile Lys Ser
1                5                10                  15 atc tat aat aat caa tct tta aca gca aca tca ggt ggt aat ggt atc     914
Ile Tyr Asn Asn Gln Ser Leu Thr Ala Thr Ser Gly Gly Asn Gly Ile
            20              25              30 aaa gta gct gtg ctt gat aca ggt gtt tat aca aat cat att gat tta     962
Lys Val Ala Val Leu Asp Thr Gly Val Tyr Thr Asn His Ile Asp Leu
        35              40              45 gca gga tca gca gaa cag tgt aaa gac ttt aca caa tca agc cca ctt    1010
Ala Gly Ser Ala Glu Gln Cys Lys Asp Phe Thr Gln Ser Ser Pro Leu
    50              55              60 gta aat ggt tct tgt act gat cgt caa gga cat ggt aca cat gta gca    1058
Val Asn Gly Ser Cys Thr Asp Arg Gln Gly His Gly Thr His Val Ala
65              70              75              80 gga act gtt tta gca cat ggt ggt agt gat gga caa ggt gtt tac gga    1106
Gly Thr Val Leu Ala His Gly Gly Ser Asp Gly Gln Gly Val Tyr Gly
                85              90              95 gta gct cct gat gcg aag cta tgg gca tat aaa gtg tta ggt gat aac    1154
Val Ala Pro Asp Ala Lys Leu Trp Ala Tyr Lys Val Leu Gly Asp Asn
            100             105             110 ggt tct ggt tat tca gat gat atc gct gca gcg att aga cat gta gca    1202
Gly Ser Gly Tyr Ser Asp Asp Ile Ala Ala Ala Ile Arg His Val Ala
        115             120             125 gat caa gca act agc aca ggc tct aaa gta gtt att aat atg tct ctt    1250
Asp Gln Ala Thr Ser Thr Gly Ser Lys Val Val Ile Asn Met Ser Leu
    130             135             140 ggc tct tct ggt aaa gat tca ctc atc tca agt gca gta gac tat gca    1298
Gly Ser Ser Gly Lys Asp Ser Leu Ile Ser Ser Ala Val Asp Tyr Ala
145             150             155             160 tac aat aaa ggt gta tta gtt gtt gct gcg gca gga aac agt ggt tca    1346
Tyr Asn Lys Gly Val Leu Val Val Ala Ala Ala Gly Asn Ser Gly Ser
                165             170             175 ggt agt aat aca att ggt tat cca gga gca ttg gtc aat gca gtt gcc    1394
Gly Ser Asn Thr Ile Gly Tyr Pro Gly Ala Leu Val Asn Ala Val Ala
            180             185             190 gtt gca gct tta gag aat gtg caa caa aat ggg act tat cgc gta gcg    1442
Val Ala Ala Leu Glu Asn Val Gln Gln Asn Gly Thr Tyr Arg Val Ala
        195             200             205
```

-continued

| | | | |
|---|---|---|---|
| aat ttc tca tca aga ggt aac cca tca act gat gga gat tat gtc atc<br>Asn Phe Ser Ser Arg Gly Asn Pro Ser Thr Asp Gly Asp Tyr Val Ile<br>210                                    215                          220 | 1490 |

```
aat ttc tca tca aga ggt aac cca tca act gat gga gat tat gtc atc    1490
Asn Phe Ser Ser Arg Gly Asn Pro Ser Thr Asp Gly Asp Tyr Val Ile
210                 215                 220 caa gag cgt gat att gaa gtg tct gcc cca ggt gca gca gtg gaa tcc    1538
Gln Glu Arg Asp Ile Glu Val Ser Ala Pro Gly Ala Ala Val Glu Ser
225                 230                 235                 240 act tgg tat aat ggc ggt tat aac aca att agt ggt act tct atg gct    1586
Thr Trp Tyr Asn Gly Gly Tyr Asn Thr Ile Ser Gly Thr Ser Met Ala
                245                 250                 255 aca cca cat gta gct ggt tta gca gca aag att tgg gct tcg aac cct    1634
Thr Pro His Val Ala Gly Leu Ala Ala Lys Ile Trp Ala Ser Asn Pro
            260                 265                 270 tca tgg agt aaa tct act tta aga aca gaa tta caa aat cgt gcc aag    1682
Ser Trp Ser Lys Ser Thr Leu Arg Thr Glu Leu Gln Asn Arg Ala Lys
        275                 280                 285 gtt tat gat att aaa ggt ggc gtt ggt gca aca aca ggc gat gac tat    1730
Val Tyr Asp Ile Lys Gly Gly Val Gly Ala Thr Thr Gly Asp Asp Tyr
    290                 295                 300 gca tca gga ttt ggt tac cct aga gta aaa taattagaat aggggttgct      1780
Ala Ser Gly Phe Gly Tyr Pro Arg Val Lys
305                 310 atattcaaat agcaacctct tttgtatatg attatgacgt gctagaattc tttaaaaact  1840
taggattttt cataaccgaa acgagaagga taaccccgct tgcaatgagt aatagacttg  1900
tagtaataaa acggcagta aatccaaagg ccccagcaac cattcctccc ataacaggtc   1960
caatcacatt tcctagaaat cttaaactgg tattatatcc cagcacctct ccttgcatgg  2020
ctataggtgc agcctgtcta atataggcaa tacgcacagg tataattcct ccaatagtta  2080
ccccgagtgc aaaacgaatg ataataagct gccacatttc agtgacaaat ccacctggaa  2140
aatagacgat accagctaaa acaataagg ccattaatat tttaatataa ccataattgt   2200
ccccaagctt tccccaagtt tttgacatca ttaagttacc tacaccagct gcagaaaaag  2260
caa                                                               2263
```

<210> SEQ ID NO 6
<211> LENGTH: 420
<212> TYPE: PRT
<213> ORGANISM: Bacillus sp.

<400> SEQUENCE: 6

```
Met Thr  Lys Lys Lys Thr Val  Ala Ala Ala Leu Leu Ser Leu Thr Leu
        -105                -100                -95

Gly Met Ser Val Phe Thr Ser Gly Ile Ser Ala Gln Val Ser Asp Glu
-90                 -85                 -80                 -75

Ala Lys Gly Ser Glu Thr Tyr Arg Val Leu Ile Gln Ala Pro Ser Asn
                -70                 -65                 -60

Ser Val Asn Ala Leu Glu Thr Lys Tyr Glu Lys Arg Trp Asp Phe Gly
            -55                 -50                 -45

Lys Glu Gly Phe Thr Ala Asp Val Asn Ala Lys Glu Leu Gln Thr Leu
        -40                 -35                 -30

Gln Ala Thr Lys Asn Val Glu Val Gln Lys Val Asn Glu Met Ser Ile
    -25                 -20                 -15

Ala Thr Val Thr Gly Glu Val Ser Lys Ala Glu Val Thr Ala Val Pro
-10                 -5                  -1  1                5

Ser Ser Gln Thr Pro Trp Gly Ile Lys Ser Ile Tyr Asn Asn Gln Ser
                10                  15                  20
```

```
Leu Thr Ala Thr Ser Gly Gly Asn Gly Ile Lys Val Ala Val Leu Asp
             25                  30                  35

Thr Gly Val Tyr Thr Asn His Ile Asp Leu Ala Gly Ser Ala Glu Gln
         40                  45                  50

Cys Lys Asp Phe Thr Gln Ser Ser Pro Leu Val Asn Gly Ser Cys Thr
 55                  60                  65                  70

Asp Arg Gln Gly His Gly Thr His Val Ala Gly Thr Val Leu Ala His
                 75                  80                  85

Gly Gly Ser Asp Gly Gln Gly Val Tyr Gly Val Ala Pro Asp Ala Lys
             90                  95                 100

Leu Trp Ala Tyr Lys Val Leu Gly Asp Asn Gly Ser Gly Tyr Ser Asp
        105                 110                 115

Asp Ile Ala Ala Ala Ile Arg His Val Ala Asp Gln Ala Thr Ser Thr
    120                 125                 130

Gly Ser Lys Val Val Ile Asn Met Ser Leu Gly Ser Ser Gly Lys Asp
135                 140                 145                 150

Ser Leu Ile Ser Ser Ala Val Asp Tyr Ala Tyr Asn Lys Gly Val Leu
                155                 160                 165

Val Val Ala Ala Ala Gly Asn Ser Gly Ser Gly Ser Asn Thr Ile Gly
            170                 175                 180

Tyr Pro Gly Ala Leu Val Asn Ala Val Ala Val Ala Ala Leu Glu Asn
        185                 190                 195

Val Gln Gln Asn Gly Thr Tyr Arg Val Ala Asn Phe Ser Ser Arg Gly
    200                 205                 210

Asn Pro Ser Thr Asp Gly Asp Tyr Val Ile Gln Glu Arg Asp Ile Glu
215                 220                 225                 230

Val Ser Ala Pro Gly Ala Ala Val Glu Ser Thr Trp Tyr Asn Gly Gly
                235                 240                 245

Tyr Asn Thr Ile Ser Gly Thr Ser Met Ala Thr Pro His Val Ala Gly
            250                 255                 260

Leu Ala Ala Lys Ile Trp Ala Ser Asn Pro Ser Trp Ser Lys Ser Thr
        265                 270                 275

Leu Arg Thr Glu Leu Gln Asn Arg Ala Lys Val Tyr Asp Ile Lys Gly
    280                 285                 290

Gly Val Gly Ala Thr Thr Gly Asp Asp Tyr Ala Ser Gly Phe Gly Tyr
295                 300                 305                 310

Pro Arg Val Lys

<210> SEQ ID NO 7
<211> LENGTH: 313
<212> TYPE: PRT
<213> ORGANISM: Bacillus sp.

<400> SEQUENCE: 7

Ala Ala Gly Tyr Pro Ser Asp Gln Thr Pro Trp Gly Ile Ala Ser Ile
 1               5                  10                  15

Tyr Asn Asn Ser Ser Ile Thr Ser Thr Ser Gly Gly Ser Gly Ile Lys
                20                  25                  30

Val Ala Val Leu Asp Thr Gly Val Tyr Thr Gly His Ile Asp Leu Glu
            35                  40                  45

Gly Ser Ala Glu Gln Cys Lys Asp Phe Thr Gln Ser Thr Pro Leu Val
        50                  55                  60

Asn Gly Ser Cys Thr Asp Arg Gln Gly His Gly Thr His Val Ala Gly
 65                  70                  75                  80
```

-continued

```
Thr Val Leu Ala His Gly Gly Tyr Asp Gly Gln Gly Ile Tyr Gly Val
                85                  90                  95
Ala Pro Gln Ala Lys Leu Trp Ala Tyr Lys Val Leu Gly Asp Asn Gly
            100                 105                 110
Ser Gly Tyr Ser Asp Asp Ile Ala Gly Ala Ile Arg His Val Ala Asp
            115                 120                 125
Glu Ala Ser Arg Thr Gly Ser Lys Val Val Ile Asn Met Ser Leu Gly
130                 135                 140
Ser Ser Gly Lys Asp Ser Leu Ile Ser Ser Ala Val Asp Tyr Ala Tyr
145                 150                 155                 160
Ser Lys Gly Val Leu Val Ala Ala Ala Gly Asn Ser Gly Tyr Ser
                165                 170                 175
Ala Asn Thr Ile Gly Tyr Pro Gly Ala Leu Lys Asn Ala Ile Ala Val
            180                 185                 190
Ala Ala Leu Glu Asn Val Gln Gln Asn Gly Thr Tyr Arg Val Ala Asn
            195                 200                 205
Phe Ser Ser Arg Gly Asn Pro Asn Thr Asp Gly Asp Tyr Ile Ile Gln
210                 215                 220
Glu Lys Asp Val Glu Val Ser Ala Pro Gly Ala Ser Ile Glu Ser Thr
225                 230                 235                 240
Trp Tyr Asn Gly Gly Tyr Asn Thr Ile Ser Gly Thr Ser Met Ala Thr
                245                 250                 255
Pro His Val Ala Gly Leu Ala Ala Lys Ile Trp Ser Ser Pro Ser
            260                 265                 270
Met Ser His Thr Gln Leu Arg Thr Glu Leu Gln Asn Arg Ala Lys Gln
            275                 280                 285
Tyr Asp Ile Lys Gly Gly Tyr Gly Ala Ala Thr Gly Asp Asp Tyr Ala
290                 295                 300
Ser Gly Phe Gly Tyr Pro Arg Val Lys
305                 310

<210> SEQ ID NO 8
<211> LENGTH: 314
<212> TYPE: PRT
<213> ORGANISM: bacillus idriensis

<400> SEQUENCE: 8

Lys Thr Met Ala Leu Pro Ser Thr Arg Thr Pro Trp Gly Ile Lys Ala
1               5                   10                  15
Ile Tyr Asn Asn Ser Ser Leu Thr Ser Thr Gly Gly Asp Gly Ile
                20                  25                  30
Lys Ile Ala Val Leu Asp Thr Gly Val Gln Thr Ser His Ile Asp Leu
            35                  40                  45
Ser Gln Asn Val Glu Gln Cys Lys Asp Phe Thr Val Gly Ser Ser Tyr
        50                  55                  60
Thr Asn Gly Ser Cys Thr Asp Arg Asn Gly His Gly Thr His Val Ala
65                  70                  75                  80
Gly Thr Ala Leu Ala Asn Gly Gly Ser Asp Gly Met Gly Ile Tyr Gly
                85                  90                  95
Val Ala Pro Gln Ser Glu Leu Trp Ala Tyr Lys Val Leu Thr Asp Ser
            100                 105                 110
Gly Ser Gly Tyr Ser Asp Asp Ile Ala Ala Ile Arg His Ala Ala
            115                 120                 125
Asp Glu Gly Thr Arg Thr Gly Ser Lys Val Ile Ile Ser Met Ser Leu
130                 135                 140
```

```
Gly Ser Ser Gly Lys Asp Ser Leu Ile Ala Ser Ala Val Asp Tyr Ala
145                 150                 155                 160

Tyr Gly Lys Gly Ala Leu Val Ile Ala Ala Gly Asn Ser Gly Ser
            165                 170                 175

Gly Asn Asn Thr Ile Gly Tyr Pro Gly Ala Leu Val Asn Ala Val Ala
                180                 185                 190

Val Ala Ala Leu Glu Asn Val Gln Gln Asn Gly Thr Tyr Arg Val Ala
            195                 200                 205

Asn Phe Ser Ser Arg Gly Asn Ser Ala Thr Asp Gly Asp Phe Ile Ile
        210                 215                 220

Gly Glu Arg Asp Val Glu Ile Ser Ala Pro Gly Ala Ser Ile Glu Ser
225                 230                 235                 240

Thr Trp Ile Asn Ser Gly Tyr Asn Thr Ile Ser Gly Thr Ser Met Ala
                245                 250                 255

Thr Pro His Val Ser Gly Leu Ala Ala Lys Ile Trp Ser Ser Asn Lys
            260                 265                 270

Ser Gln Ser Asn Val Gln Val Arg Ala Glu Leu Gln Asn Arg Ala Lys
        275                 280                 285

Leu Tyr Asp Ile Lys Gly Gly Ile Gly Ala Ala Thr Gly Asp Asp His
290                 295                 300

Ala Ser Gly Phe Gly Phe Ala Arg Val Gln
305                 310

<210> SEQ ID NO 9
<211> LENGTH: 314
<212> TYPE: PRT
<213> ORGANISM: Bacillus sp.

<400> SEQUENCE: 9

Glu Val Thr Ala Val Pro Ser Ser Gln Thr Pro Trp Gly Ile Lys Ser
1               5                   10                  15

Ile Tyr Asn Asn Gln Ser Leu Thr Ala Thr Ser Gly Gly Asn Gly Ile
            20                  25                  30

Lys Val Ala Val Leu Asp Thr Gly Val Tyr Thr Asn His Ile Asp Leu
        35                  40                  45

Ala Gly Ser Ala Glu Gln Cys Lys Asp Phe Thr Gln Ser Ser Pro Leu
50                  55                  60

Val Asn Gly Ser Cys Thr Asp Arg Gln Gly His Gly Thr His Val Ala
65                  70                  75                  80

Gly Thr Val Leu Ala His Gly Gly Ser Asp Gly Gln Gly Val Tyr Gly
                85                  90                  95

Val Ala Pro Asp Ala Lys Leu Trp Ala Tyr Lys Val Leu Gly Asp Asn
            100                 105                 110

Gly Ser Gly Tyr Ser Asp Ile Ala Ala Ala Ile Arg His Val Ala
        115                 120                 125

Asp Gln Ala Thr Ser Thr Gly Ser Lys Val Val Ile Asn Met Ser Leu
    130                 135                 140

Gly Ser Ser Gly Lys Asp Ser Leu Ile Ser Ser Ala Val Asp Tyr Ala
145                 150                 155                 160

Tyr Asn Lys Gly Val Leu Val Val Ala Ala Gly Asn Ser Gly Ser
            165                 170                 175

Gly Ser Asn Thr Ile Gly Tyr Pro Gly Ala Leu Val Asn Ala Val Ala
                180                 185                 190

Val Ala Ala Leu Glu Asn Val Gln Gln Asn Gly Thr Tyr Arg Val Ala
            195                 200                 205
```

```
Asn Phe Ser Ser Arg Gly Asn Pro Ser Thr Asp Gly Asp Tyr Val Ile
    210                 215                 220

Gln Glu Arg Asp Ile Glu Val Ser Ala Pro Gly Ala Ala Val Glu Ser
225                 230                 235                 240

Thr Trp Tyr Asn Gly Gly Tyr Asn Thr Ile Ser Gly Thr Ser Met Ala
                245                 250                 255

Thr Pro His Val Ala Gly Leu Ala Ala Lys Ile Trp Ala Ser Asn Pro
            260                 265                 270

Ser Trp Ser Lys Ser Thr Leu Arg Thr Glu Leu Gln Asn Arg Ala Lys
        275                 280                 285

Val Tyr Asp Ile Lys Gly Val Gly Ala Thr Thr Gly Asp Asp Tyr
290                 295                 300

Ala Ser Gly Phe Gly Tyr Pro Arg Val Lys
305                 310

<210> SEQ ID NO 10
<211> LENGTH: 311
<212> TYPE: PRT
<213> ORGANISM: Bacillus sp.

<400> SEQUENCE: 10

Ala Val Pro Ser Thr Gln Thr Pro Trp Gly Ile Lys Ser Ile Tyr Asn
1               5                   10                  15

Asp Gln Ser Ile Thr Lys Thr Gly Gly Ser Gly Ile Lys Val Ala
            20                  25                  30

Val Leu Asp Thr Gly Val Tyr Thr Ser His Leu Asp Leu Ala Gly Ser
            35                  40                  45

Ala Glu Gln Cys Lys Asp Phe Thr Gln Ser Asn Pro Leu Val Asp Gly
50                  55                  60

Ser Cys Thr Asp Arg Gln Gly His Gly Thr His Val Ala Gly Thr Val
65                  70                  75                  80

Leu Ala His Gly Gly Ser Asn Gly Gln Gly Val Tyr Gly Val Ala Pro
                85                  90                  95

Gln Ala Lys Leu Trp Ala Tyr Lys Val Leu Gly Asp Asn Gly Ser Gly
            100                 105                 110

Tyr Ser Asp Asp Ile Ala Ala Ala Ile Arg His Val Ala Asp Glu Ala
            115                 120                 125

Ser Arg Thr Gly Ser Lys Val Val Ile Asn Met Ser Leu Gly Ser Ser
            130                 135                 140

Ala Lys Asp Ser Leu Ile Ala Ser Ala Val Asp Tyr Ala Tyr Gly Lys
145                 150                 155                 160

Gly Val Leu Ile Val Ala Ala Ala Gly Asn Ser Gly Ser Gly Ser Asn
                165                 170                 175

Thr Ile Gly Phe Pro Gly Gly Leu Val Asn Ala Val Ala Val Ala Ala
            180                 185                 190

Leu Glu Asn Val Gln Gln Asn Gly Thr Tyr Arg Val Ala Asp Phe Ser
            195                 200                 205

Ser Arg Gly Asn Pro Ala Thr Ala Gly Asp Tyr Ile Ile Gln Glu Arg
    210                 215                 220

Asp Ile Glu Val Ser Ala Pro Gly Ala Ser Val Glu Ser Thr Trp Tyr
225                 230                 235                 240

Thr Gly Gly Tyr Asn Thr Ile Ser Gly Thr Ser Met Ala Thr Pro His
                245                 250                 255

Val Ala Gly Leu Ala Ala Lys Ile Trp Ser Ala Asn Thr Ser Leu Ser
            260                 265                 270
```

His Ser Gln Leu Arg Thr Glu Leu Gln Asn Arg Ala Lys Val Tyr Asp
            275                 280                 285

Ile Lys Gly Gly Ile Gly Ala Gly Thr Gly Asp Asp Tyr Ala Ser Gly
        290                 295                 300

Phe Gly Tyr Pro Arg Val Lys
305                 310

<210> SEQ ID NO 11
<211> LENGTH: 41
<212> TYPE: DNA
<213> ORGANISM: Artificial sequence
<220> FEATURE:
<223> OTHER INFORMATION: Synthetic construct

<400> SEQUENCE: 11
gttcatcgat cgcatcggct aaagaaccgg agacccaaaa t                41

<210> SEQ ID NO 12
<211> LENGTH: 48
<212> TYPE: DNA
<213> ORGANISM: Artificial sequence
<220> FEATURE:
<223> OTHER INFORMATION: Synthetic construct

<400> SEQUENCE: 12
gcgttttttt attgattaac gcgtttattt tacacgtggg tatccgaa        48

<210> SEQ ID NO 13
<211> LENGTH: 42
<212> TYPE: DNA
<213> ORGANISM: Artificial sequence
<220> FEATURE:
<223> OTHER INFORMATION: Synthetic construct

<400> SEQUENCE: 13
gttcatcgat cgcatcggct caagatgcgg caaaaacaga tg              42

<210> SEQ ID NO 14
<211> LENGTH: 47
<212> TYPE: DNA
<213> ORGANISM: Artificial sequence
<220> FEATURE:
<223> OTHER INFORMATION: Synthetic construct

<400> SEQUENCE: 14
gcgttttttt attgattaac gcgtttattg tactctggca aacccaa         47

<210> SEQ ID NO 15
<211> LENGTH: 43
<212> TYPE: DNA
<213> ORGANISM: Artificial sequence
<220> FEATURE:
<223> OTHER INFORMATION: Synthetic construct

<400> SEQUENCE: 15
ttttagttca tcgatcgcat cggcttcaga tgaagcaaag ggg             43

<210> SEQ ID NO 16
<211> LENGTH: 48
<212> TYPE: DNA
<213> ORGANISM: Artificial sequence
<220> FEATURE:
<223> OTHER INFORMATION: Synthetic construct

<400> SEQUENCE: 16
gcgtttagtg gtgatggtga tgatgttta ctctagggta accaaatc         48

<210> SEQ ID NO 17
<211> LENGTH: 269
<212> TYPE: PRT
<213> ORGANISM: Bacillus lentus

<400> SEQUENCE: 17

```
Ala Gln Ser Val Pro Trp Gly Ile Ser Arg Val Gln Ala Pro Ala Ala
1               5                   10                  15

His Asn Arg Gly Leu Thr Gly Ser Gly Val Lys Val Ala Val Leu Asp
            20                  25                  30

Thr Gly Ile Ser Thr His Pro Asp Leu Asn Ile Arg Gly Gly Ala Ser
        35                  40                  45

Phe Val Pro Gly Glu Pro Ser Thr Gln Asp Gly Asn Gly His Gly Thr
    50                  55                  60

His Val Ala Gly Thr Ile Ala Ala Leu Asn Asn Ser Ile Gly Val Leu
65                  70                  75                  80

Gly Val Ala Pro Ser Ala Glu Leu Tyr Ala Val Lys Val Leu Gly Ala
                85                  90                  95

Ser Gly Ser Gly Ser Val Ser Ser Ile Ala Gln Gly Leu Glu Trp Ala
            100                 105                 110

Gly Asn Asn Gly Met His Val Ala Asn Leu Ser Leu Gly Ser Pro Ser
        115                 120                 125

Pro Ser Ala Thr Leu Glu Gln Ala Val Asn Ser Ala Thr Ser Arg Gly
    130                 135                 140

Val Leu Val Val Ala Ala Ser Gly Asn Ser Gly Ala Gly Ser Ile Ser
145                 150                 155                 160

Tyr Pro Ala Arg Tyr Ala Asn Ala Met Ala Val Gly Ala Thr Asp Gln
                165                 170                 175

Asn Asn Asn Arg Ala Ser Phe Ser Gln Tyr Gly Ala Gly Leu Asp Ile
            180                 185                 190

Val Ala Pro Gly Val Asn Val Gln Ser Thr Tyr Pro Gly Ser Thr Tyr
        195                 200                 205

Ala Ser Leu Asn Gly Thr Ser Met Ala Thr Pro His Val Ala Gly Ala
    210                 215                 220

Ala Ala Leu Val Lys Gln Lys Asn Pro Ser Trp Ser Asn Val Gln Ile
225                 230                 235                 240

Arg Asn His Leu Lys Asn Thr Ala Thr Ser Leu Gly Ser Thr Asn Leu
                245                 250                 255

Tyr Gly Ser Gly Leu Val Asn Ala Glu Ala Ala Thr Arg
            260                 265
```

<210> SEQ ID NO 18
<211> LENGTH: 269
<212> TYPE: PRT
<213> ORGANISM: Thermomyces lanuginosus

<400> SEQUENCE: 18

```
Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45
```

```
Ala Thr Phe Leu Tyr Ser Phe Glu Asp Ser Gly Val Gly Asp Val Thr
 50                  55                  60

Gly Phe Leu Ala Leu Asp Asn Thr Asn Lys Leu Ile Val Leu Ser Phe
 65                  70                  75                  80

Arg Gly Ser Arg Ser Ile Glu Asn Trp Ile Gly Asn Leu Asn Phe Asp
                 85                  90                  95

Leu Lys Glu Ile Asn Asp Ile Cys Ser Gly Cys Arg Gly His Asp Gly
                100                 105                 110

Phe Thr Ser Ser Trp Arg Ser Val Ala Asp Thr Leu Arg Gln Lys Val
                115                 120                 125

Glu Asp Ala Val Arg Glu His Pro Asp Tyr Arg Val Val Phe Thr Gly
130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
                180                 185                 190

Leu Tyr Arg Ile Thr His Thr Asn Asp Ile Val Pro Arg Leu Pro Pro
         195                 200                 205

Arg Glu Phe Gly Tyr Ser His Ser Ser Pro Glu Tyr Trp Ile Lys Ser
210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
                260                 265

<210> SEQ ID NO 19
<211> LENGTH: 485
<212> TYPE: PRT
<213> ORGANISM: Bacillus sp.

<400> SEQUENCE: 19

His His Asn Gly Thr Asn Gly Thr Met Met Gln Tyr Phe Glu Trp Tyr
 1               5                  10                  15

Leu Pro Asn Asp Gly Asn His Trp Asn Arg Leu Arg Ser Asp Ala Ser
                 20                  25                  30

Asn Leu Lys Asp Lys Gly Ile Ser Ala Val Trp Ile Pro Pro Ala Trp
             35                  40                  45

Lys Gly Ala Ser Gln Asn Asp Val Gly Tyr Gly Ala Tyr Asp Leu Tyr
 50                  55                  60

Asp Leu Gly Glu Phe Asn Gln Lys Gly Thr Ile Arg Thr Lys Tyr Gly
 65                  70                  75                  80

Thr Arg Asn Gln Leu Gln Ala Ala Val Asn Ala Leu Lys Ser Asn Gly
                 85                  90                  95

Ile Gln Val Tyr Gly Asp Val Val Met Asn His Lys Gly Gly Ala Asp
                100                 105                 110

Ala Thr Glu Met Val Arg Ala Val Glu Val Asn Pro Asn Asn Arg Asn
                115                 120                 125

Gln Glu Val Ser Gly Glu Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160
```

His Phe Asp Gly Val Asp Trp Asp Gln Ser Arg Lys Leu Asn Asn Arg
            165                 170                 175

Ile Tyr Lys Phe Arg Gly Asp Gly Lys Gly Trp Asp Trp Glu Val Asp
        180                 185                 190

Thr Glu Asn Gly Asn Tyr Asp Tyr Leu Met Tyr Ala Asp Ile Asp Met
            195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Asn Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Gln Ile Phe Asn Gly Thr Val Val Gln Arg
305                 310                 315                 320

His Pro Met His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Lys Ser
    370                 375                 380

Lys Ile Asp Pro Ile Leu Glu Ala Arg Gln Lys Tyr Ala Tyr Gly Arg
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Asn Lys Trp Met Phe Val Gly Arg Asn Lys Ala Gly
        435                 440                 445

Gln Val Trp Thr Asp Ile Thr Gly Asn Arg Ala Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485

<210> SEQ ID NO 20
<211> LENGTH: 485
<212> TYPE: PRT
<213> ORGANISM: Bacillus halmapalus

<400> SEQUENCE: 20

His His Asn Gly Thr Asn Gly Thr Met Met Gln Tyr Phe Glu Trp His
1               5                   10                  15

Leu Pro Asn Asp Gly Asn His Trp Asn Arg Leu Arg Asp Asp Ala Ser
            20                  25                  30

Asn Leu Arg Asn Arg Gly Ile Thr Ala Ile Trp Ile Pro Pro Ala Trp
        35                  40                  45

```
Lys Gly Thr Ser Gln Asn Asp Val Gly Tyr Gly Ala Tyr Asp Leu Tyr
 50                  55                  60

Asp Leu Gly Glu Phe Asn Gln Lys Gly Thr Val Arg Thr Lys Tyr Gly
 65                  70                  75                  80

Thr Arg Ser Gln Leu Glu Ser Ala Ile His Ala Leu Lys Asn Asn Gly
                 85                  90                  95

Val Gln Val Tyr Gly Asp Val Val Met Asn His Lys Gly Gly Ala Asp
            100                 105                 110

Ala Thr Glu Asn Val Leu Ala Val Glu Val Asn Pro Asn Asn Arg Asn
        115                 120                 125

Gln Glu Ile Ser Gly Asp Tyr Thr Ile Glu Ala Trp Thr Lys Phe Asp
130                 135                 140

Phe Pro Gly Arg Gly Asn Thr Tyr Ser Asp Phe Lys Trp Arg Trp Tyr
145                 150                 155                 160

His Phe Asp Gly Val Asp Trp Asp Gln Ser Arg Gln Phe Gln Asn Arg
                165                 170                 175

Ile Tyr Lys Phe Arg Gly Asp Gly Lys Ala Trp Asp Trp Glu Val Asp
            180                 185                 190

Ser Glu Asn Gly Asn Tyr Asp Tyr Leu Met Tyr Ala Asp Val Asp Met
        195                 200                 205

Asp His Pro Glu Val Val Asn Glu Leu Arg Arg Trp Gly Glu Trp Tyr
210                 215                 220

Thr Asn Thr Leu Asn Leu Asp Gly Phe Arg Ile Asp Ala Val Lys His
225                 230                 235                 240

Ile Lys Tyr Ser Phe Thr Arg Asp Trp Leu Thr His Val Arg Asn Ala
                245                 250                 255

Thr Gly Lys Glu Met Phe Ala Val Ala Glu Phe Trp Lys Asn Asp Leu
            260                 265                 270

Gly Ala Leu Glu Asn Tyr Leu Asn Lys Thr Asn Trp Asn His Ser Val
        275                 280                 285

Phe Asp Val Pro Leu His Tyr Asn Leu Tyr Asn Ala Ser Asn Ser Gly
290                 295                 300

Gly Asn Tyr Asp Met Ala Lys Leu Leu Asn Gly Thr Val Val Gln Lys
305                 310                 315                 320

His Pro Met His Ala Val Thr Phe Val Asp Asn His Asp Ser Gln Pro
                325                 330                 335

Gly Glu Ser Leu Glu Ser Phe Val Gln Glu Trp Phe Lys Pro Leu Ala
            340                 345                 350

Tyr Ala Leu Ile Leu Thr Arg Glu Gln Gly Tyr Pro Ser Val Phe Tyr
        355                 360                 365

Gly Asp Tyr Tyr Gly Ile Pro Thr His Ser Val Pro Ala Met Lys Ala
370                 375                 380

Lys Ile Asp Pro Ile Leu Glu Ala Arg Gln Asn Phe Ala Tyr Gly Thr
385                 390                 395                 400

Gln His Asp Tyr Phe Asp His His Asn Ile Ile Gly Trp Thr Arg Glu
                405                 410                 415

Gly Asn Thr Thr His Pro Asn Ser Gly Leu Ala Thr Ile Met Ser Asp
            420                 425                 430

Gly Pro Gly Gly Glu Lys Trp Met Tyr Val Gly Gln Asn Lys Ala Gly
        435                 440                 445

Gln Val Trp His Asp Ile Thr Gly Asn Lys Pro Gly Thr Val Thr Ile
450                 455                 460
```

Asn Ala Asp Gly Trp Ala Asn Phe Ser Val Asn Gly Gly Ser Val Ser
465                 470                 475                 480

Ile Trp Val Lys Arg
            485

<210> SEQ ID NO 21
<211> LENGTH: 484
<212> TYPE: PRT
<213> ORGANISM: Bacillus sp.

<400> SEQUENCE: 21

Asn Thr Ala Pro Ile Asn Glu Thr Met Met Gln Tyr Phe Glu Trp Asp
1               5                   10                  15

Leu Pro Asn Asp Gly Thr Leu Trp Thr Lys Val Lys Asn Glu Ala Ala
            20                  25                  30

Asn Leu Ser Ser Leu Gly Ile Thr Ala Leu Trp Leu Pro Pro Ala Tyr
        35                  40                  45

Lys Gly Thr Ser Gln Ser Asp Val Gly Tyr Gly Val Tyr Asp Leu Tyr
    50                  55                  60

Asp Leu Gly Glu Phe Asn Gln Lys Gly Thr Ile Arg Thr Lys Tyr Gly
65                  70                  75                  80

Thr Lys Thr Gln Tyr Ile Gln Ala Ile Gln Ala Ala Lys Ala Ala Gly
                85                  90                  95

Met Gln Val Tyr Ala Asp Val Val Phe Asn His Lys Ala Gly Ala Asp
            100                 105                 110

Gly Thr Glu Phe Val Asp Ala Val Glu Val Asp Pro Ser Asn Arg Asn
        115                 120                 125

Gln Glu Thr Ser Gly Thr Tyr Gln Ile Gln Ala Trp Thr Lys Phe Asp
    130                 135                 140

Phe Pro Gly Arg Gly Asn Thr Tyr Ser Ser Phe Lys Trp Arg Trp Tyr
145                 150                 155                 160

His Phe Asp Gly Thr Asp Trp Asp Glu Ser Arg Lys Leu Asn Arg Ile
                165                 170                 175

Tyr Lys Phe Arg Ser Thr Gly Lys Ala Trp Asp Trp Glu Val Asp Thr
            180                 185                 190

Glu Asn Gly Asn Tyr Asp Tyr Leu Met Phe Ala Asp Leu Asp Met Asp
        195                 200                 205

His Pro Glu Val Val Thr Glu Leu Lys Asn Trp Gly Thr Trp Tyr Val
    210                 215                 220

Asn Thr Thr Asn Ile Asp Gly Phe Arg Leu Asp Ala Val Lys His Ile
225                 230                 235                 240

Lys Tyr Thr Phe Phe Pro Asp Trp Leu Thr Tyr Val Arg Asn Gln Thr
                245                 250                 255

Gly Lys Asn Leu Phe Ala Val Gly Glu Phe Trp Ser Tyr Asp Val Asn
            260                 265                 270

Lys Leu His Asn Tyr Ile Thr Lys Thr Asn Gly Ser Met Ser Leu Phe
        275                 280                 285

Asp Ala Pro Leu His Asn Asn Phe Tyr Thr Ala Ser Lys Ser Ser Gly
    290                 295                 300

Tyr Phe Asp Met Arg Tyr Leu Leu Asn Asn Thr Leu Met Lys Asp Gln
305                 310                 315                 320

Pro Ser Leu Ala Val Thr Leu Val Asp Asn His Asp Thr Gln Pro Gly
                325                 330                 335

Gln Ser Leu Gln Ser Trp Val Glu Pro Trp Phe Lys Pro Leu Ala Tyr
            340                 345                 350

```
Ala Phe Ile Leu Thr Arg Gln Glu Gly Tyr Pro Cys Val Phe Tyr Gly
            355                 360                 365

Asp Tyr Tyr Gly Ile Pro Lys Tyr Asn Ile Pro Gly Leu Lys Ser Lys
370                 375                 380

Ile Asp Pro Leu Leu Ile Ala Arg Arg Asp Tyr Ala Tyr Gly Thr Gln
385                 390                 395                 400

Arg Asp Tyr Ile Asp His Gln Asp Ile Ile Gly Trp Thr Arg Glu Gly
            405                 410                 415

Ile Asp Thr Lys Pro Asn Ser Gly Leu Ala Ala Leu Ile Thr Asp Gly
            420                 425                 430

Pro Gly Gly Ser Lys Trp Met Tyr Val Gly Lys Lys His Ala Gly Lys
            435                 440                 445

Val Phe Tyr Asp Leu Thr Gly Asn Arg Ser Asp Thr Val Thr Ile Asn
450                 455                 460

Ala Asp Gly Trp Gly Glu Phe Lys Val Asn Gly Gly Ser Val Ser Ile
465                 470                 475                 480

Trp Val Ala Lys

<210> SEQ ID NO 22
<211> LENGTH: 485
<212> TYPE: PRT
<213> ORGANISM: Cytophaga sp.

<400> SEQUENCE: 22

Ala Ala Thr Asn Gly Thr Met Met Gln Tyr Phe Glu Trp Tyr Val Pro
1               5                   10                  15

Asn Asp Gly Gln Gln Trp Asn Arg Leu Arg Thr Asp Ala Pro Tyr Leu
            20                  25                  30

Ser Ser Val Gly Ile Thr Ala Val Trp Thr Pro Pro Ala Tyr Lys Gly
        35                  40                  45

Thr Ser Gln Ala Asp Val Gly Tyr Gly Pro Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Gly Glu Leu Lys Ser Ala Val Asn Thr Leu His Ser Asn Gly Ile Gln
                85                  90                  95

Val Tyr Gly Asp Val Val Met Asn His Lys Ala Gly Ala Asp Tyr Thr
            100                 105                 110

Glu Asn Val Thr Ala Val Glu Val Asn Pro Ser Asn Arg Asn Gln Glu
        115                 120                 125

Thr Ser Gly Glu Tyr Asn Ile Gln Ala Trp Thr Gly Phe Asn Phe Pro
    130                 135                 140

Gly Arg Gly Thr Thr Tyr Ser Asn Phe Lys Trp Gln Trp Phe His Phe
145                 150                 155                 160

Asp Gly Thr Asp Trp Asp Gln Ser Arg Ser Leu Ser Arg Ile Phe Lys
                165                 170                 175

Phe Arg Gly Thr Gly Lys Ala Trp Asp Trp Glu Val Ser Ser Glu Asn
            180                 185                 190

Gly Asn Tyr Asp Tyr Leu Met Tyr Ala Asp Ile Asp Tyr Asp His Pro
        195                 200                 205

Asp Val Val Asn Glu Met Lys Lys Trp Gly Val Trp Tyr Ala Asn Glu
    210                 215                 220

Val Gly Leu Asp Gly Tyr Arg Leu Asp Ala Val Lys His Ile Lys Phe
225                 230                 235                 240
```

```
Ser Phe Leu Lys Asp Trp Val Asp Asn Ala Arg Ala Ala Thr Gly Lys
            245                 250                 255

Glu Met Phe Thr Val Gly Glu Tyr Trp Gln Asn Asp Leu Gly Ala Leu
        260                 265                 270

Asn Asn Tyr Leu Ala Lys Val Asn Tyr Asn Gln Ser Leu Phe Asp Ala
            275                 280                 285

Pro Leu His Tyr Asn Phe Tyr Ala Ala Ser Thr Gly Gly Tyr Tyr
        290                 295                 300

Asp Met Arg Asn Ile Leu Asn Asn Thr Leu Val Ala Ser Asn Pro Thr
305                 310                 315                 320

Lys Ala Val Thr Leu Val Glu Asn His Asp Thr Gln Pro Gly Gln Ser
                325                 330                 335

Leu Glu Ser Thr Val Gln Pro Trp Phe Lys Pro Leu Ala Tyr Ala Phe
            340                 345                 350

Ile Leu Thr Arg Ser Gly Gly Tyr Pro Ser Val Phe Tyr Gly Asp Met
            355                 360                 365

Tyr Gly Thr Lys Gly Thr Thr Thr Arg Glu Ile Pro Ala Leu Lys Ser
        370                 375                 380

Lys Ile Glu Pro Leu Leu Lys Ala Arg Lys Asp Tyr Ala Tyr Gly Thr
385                 390                 395                 400

Gln Arg Asp Tyr Ile Asp Asn Pro Asp Val Ile Gly Trp Thr Arg Glu
                405                 410                 415

Gly Asp Ser Thr Lys Ala Lys Ser Gly Leu Ala Thr Val Ile Thr Asp
            420                 425                 430

Gly Pro Gly Gly Ser Lys Arg Met Tyr Val Gly Thr Ser Asn Ala Gly
        435                 440                 445

Glu Ile Trp Tyr Asp Leu Thr Gly Asn Arg Thr Asp Lys Ile Thr Ile
    450                 455                 460

Gly Ser Asp Gly Tyr Ala Thr Phe Pro Val Asn Gly Gly Ser Val Ser
465                 470                 475                 480

Val Trp Val Gln Gln
            485

<210> SEQ ID NO 23
<211> LENGTH: 485
<212> TYPE: PRT
<213> ORGANISM: Bacillus sp.

<400> SEQUENCE: 23

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125
```

```
Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335

Glu Glu Ala Leu Glu Ser Phe Val Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485
```

<210> SEQ ID NO 24
<211> LENGTH: 483
<212> TYPE: PRT
<213> ORGANISM: Bacillus sp.

<400> SEQUENCE: 24

```
His His Asn Gly Thr Asn Gly Thr Met Met Gln Tyr Phe Glu Trp Tyr
1               5                   10                  15
Leu Pro Asn Asp Gly Asn His Trp Asn Arg Leu Asn Ser Asp Ala Ser
            20                  25                  30
Asn Leu Lys Ser Lys Gly Ile Thr Ala Val Trp Ile Pro Pro Ala Trp
        35                  40                  45
Lys Gly Ala Ser Gln Asn Asp Val Gly Tyr Gly Ala Tyr Asp Leu Tyr
    50                  55                  60
Asp Leu Gly Glu Phe Asn Gln Lys Gly Thr Val Arg Thr Lys Tyr Gly
65                  70                  75                  80
Thr Arg Ser Gln Leu Gln Ala Ala Val Thr Ser Leu Lys Asn Asn Gly
            85                  90                  95
Ile Gln Val Tyr Gly Asp Val Val Met Asn His Lys Gly Gly Ala Asp
        100                 105                 110
Ala Thr Glu Met Val Arg Ala Val Glu Val Asn Pro Asn Asn Arg Asn
    115                 120                 125
Gln Glu Val Thr Gly Glu Tyr Thr Ile Glu Ala Trp Thr Arg Phe Asp
130                 135                 140
Phe Pro Gly Arg Gly Asn Thr His Ser Ser Phe Lys Trp Arg Trp Tyr
145                 150                 155                 160
His Phe Asp Gly Val Asp Trp Asp Gln Ser Arg Arg Leu Asn Asn Arg
            165                 170                 175
Ile Tyr Lys Phe Arg Gly Lys Ala Trp Asp Trp Glu Val Asp Thr Glu
        180                 185                 190
Asn Gly Asn Tyr Asp Tyr Leu Met Tyr Ala Asp Ile Asp Met Asp His
    195                 200                 205
Pro Glu Val Val Asn Glu Leu Arg Asn Trp Gly Val Trp Tyr Thr Asn
210                 215                 220
Thr Leu Gly Leu Asp Gly Phe Arg Ile Asp Ala Val Lys His Ile Lys
225                 230                 235                 240
Tyr Ser Phe Thr Arg Asp Trp Ile Asn His Val Arg Ser Ala Thr Gly
            245                 250                 255
Lys Asn Met Phe Ala Val Ala Glu Phe Trp Lys Asn Asp Leu Gly Ala
        260                 265                 270
Ile Glu Asn Tyr Leu Gln Lys Thr Asn Trp Asn His Ser Val Phe Asp
    275                 280                 285
Val Pro Leu His Tyr Asn Leu Tyr Asn Ala Ser Lys Ser Gly Gly Asn
290                 295                 300
Tyr Asp Met Arg Asn Ile Phe Asn Gly Thr Val Val Gln Arg His Pro
305                 310                 315                 320
Ser His Ala Val Thr Phe Val Asp Asn His Asp Ser Gln Pro Glu Glu
            325                 330                 335
Ala Leu Glu Ser Phe Val Glu Glu Trp Phe Lys Pro Leu Ala Tyr Ala
        340                 345                 350
Leu Thr Leu Thr Arg Glu Gln Gly Tyr Pro Ser Val Phe Tyr Gly Asp
    355                 360                 365
Tyr Tyr Gly Ile Pro Thr His Gly Val Pro Ala Met Arg Ser Lys Ile
370                 375                 380
Asp Pro Ile Leu Glu Ala Arg Gln Lys Tyr Ala Tyr Gly Pro Gln His
385                 390                 395                 400
Asp Tyr Leu Asp His Pro Asp Val Ile Gly Trp Thr Arg Glu Gly Asp
            405                 410                 415
```

```
Ser Ser His Pro Lys Ser Gly Leu Ala Thr Leu Ile Thr Asp Gly Pro
            420                 425                 430

Gly Gly Ser Lys Arg Met Tyr Ala Gly Leu Lys Asn Ala Gly Glu Thr
        435                 440                 445

Trp Tyr Asp Ile Thr Gly Asn Arg Ser Asp Thr Val Lys Ile Gly Ser
450                 455                 460

Asp Gly Trp Gly Glu Phe His Val Asn Asp Gly Ser Val Ser Ile Tyr
465                 470                 475                 480

Val Gln Lys

<210> SEQ ID NO 25
<211> LENGTH: 485
<212> TYPE: PRT
<213> ORGANISM: Bacillus sp.

<400> SEQUENCE: 25

His His Asn Gly Thr Asn Gly Thr Met Met Gln Tyr Phe Glu Trp Tyr
1               5                   10                  15

Leu Pro Asn Asp Gly Asn His Trp Asn Arg Leu Arg Ser Asp Ala Ser
            20                  25                  30

Asn Leu Lys Asp Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
50                  55                  60

Asp Leu Gly Glu Phe Asn Gln Lys Gly Thr Val Arg Thr Lys Tyr Gly
65                  70                  75                  80

Thr Arg Asn Gln Leu Gln Ala Ala Val Thr Ala Leu Lys Ser Asn Gly
                85                  90                  95

Ile Gln Val Tyr Gly Asp Val Val Met Asn His Lys Gly Gly Ala Asp
            100                 105                 110

Ala Thr Glu Trp Val Arg Ala Val Glu Val Asn Pro Ser Asn Arg Asn
        115                 120                 125

Gln Glu Val Ser Gly Asp Tyr Thr Ile Glu Ala Trp Thr Lys Phe Asp
130                 135                 140

Phe Pro Gly Arg Gly Asn Thr His Ser Asn Phe Lys Trp Arg Trp Tyr
145                 150                 155                 160

His Phe Asp Gly Val Asp Trp Asp Gln Ser Arg Gln Leu Gln Asn Arg
                165                 170                 175

Ile Tyr Lys Phe Arg Gly Asp Gly Lys Gly Trp Asp Trp Glu Val Asp
            180                 185                 190

Thr Glu Asn Gly Asn Tyr Asp Tyr Leu Met Tyr Ala Asp Ile Asp Met
        195                 200                 205

Asp His Pro Glu Val Val Asn Glu Leu Arg Asn Trp Gly Val Trp Tyr
210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Leu Thr His Val Arg Asn Thr
                245                 250                 255

Thr Gly Lys Asn Met Phe Ala Val Ala Glu Phe Trp Lys Asn Asp Ile
            260                 265                 270

Gly Ala Ile Glu Asn Tyr Leu Ser Lys Thr Asn Trp Asn His Ser Val
        275                 280                 285

Phe Asp Val Pro Leu His Tyr Asn Leu Tyr Asn Ala Ser Arg Ser Gly
290                 295                 300
```

```
Gly Asn Tyr Asp Met Arg Gln Ile Phe Asn Gly Thr Val Val Gln Arg
305                 310                 315                 320

His Pro Thr His Ala Val Thr Phe Val Asp Asn His Asp Ser Gln Pro
                325                 330                 335

Glu Glu Ala Leu Glu Ser Phe Val Glu Glu Trp Phe Lys Pro Leu Ala
            340                 345                 350

Cys Ala Leu Thr Leu Thr Arg Asp Gln Gly Tyr Pro Ser Val Phe Tyr
            355                 360                 365

Gly Asp Tyr Tyr Gly Ile Pro Thr His Gly Val Pro Ala Met Lys Ser
        370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Met Ile Gly Trp Thr Arg Glu
                405                 410                 415

Gly Asn Thr Ala His Pro Asn Ser Gly Leu Ala Thr Ile Met Ser Asp
            420                 425                 430

Gly Pro Gly Gly Asn Lys Trp Met Tyr Val Gly Arg Asn Lys Ala Gly
        435                 440                 445

Gln Val Trp Arg Asp Ile Thr Gly Asn Arg Ser Gly Thr Val Thr Ile
450                 455                 460

Asn Ala Asp Gly Trp Gly Asn Phe Ser Val Asn Gly Gly Ser Val Ser
465                 470                 475                 480

Ile Trp Val Asn Asn
                485

<210> SEQ ID NO 26
<211> LENGTH: 27
<212> TYPE: PRT
<213> ORGANISM: Bacillus sp.

<400> SEQUENCE: 26

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 27
<211> LENGTH: 6
<212> TYPE: PRT
<213> ORGANISM: Bacillus sp.

<400> SEQUENCE: 27

His His His His His His
1               5
```